(12) United States Patent
Arnould et al.

(10) Patent No.: US 6,486,156 B1
(45) Date of Patent: Nov. 26, 2002

(54) CHEMICAL COMPOUNDS

(75) Inventors: Jean-Claude Arnould, Reims Cedex 2 (FR); Annie Antoinette Christiane Olivier, Reims Cedex 2 (FR)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/869,064

(22) PCT Filed: Dec. 17, 1999

(86) PCT No.: PCT/GB99/04308

§ 371 (c)(1),
(2), (4) Date: Sep. 21, 2001

(87) PCT Pub. No.: WO00/39716

PCT Pub. Date: Jul. 6, 2000

(30) Foreign Application Priority Data

| Dec. 23, 1998 | (EP) | ............................................. 98403279 |
| Dec. 23, 1998 | (EP) | ............................................. 98403280 |
| Dec. 23, 1998 | (EP) | ............................................. 98403281 |
| Feb. 9, 1999 | (EP) | ............................................. 99400297 |

(51) Int. Cl.$^7$ ................. C07D 413/14; A61K 31/5377; A61P 35/00
(52) U.S. Cl. ............................... 514/235.8; 514/252.05; 514/400; 514/406; 544/124; 544/134; 544/238; 546/210; 548/335.1; 548/335.5; 548/341.1; 548/342.1; 548/343.1
(58) Field of Search ......................... 548/335.1, 335.5, 548/341.1, 342.1, 343.1; 514/400, 406, 235.8, 252.05; 544/124; 546/210, 134, 238

(56) References Cited

U.S. PATENT DOCUMENTS

| 4,333,947 A | * | 6/1982 | Karjalainen et al. ........ 548/400 |
| 6,342,765 B1 | | 1/2002 | Arnould ..................... 314/341 |

FOREIGN PATENT DOCUMENTS

| WO | WO 96/30015 | | 10/1996 |
| WO | WO 97/17070 | * | 5/1997 |
| WO | WO 98/32741 | | 7/1998 |
| WO | WO 98/37070 | | 8/1998 |
| WO | WO 99/20612 | | 4/1999 |

* cited by examiner

*Primary Examiner*—Joseph K. McKane
*Assistant Examiner*—Kamal Saeed
(74) *Attorney, Agent, or Firm*—Morgan, Lewis & Bockius LLP

(57) ABSTRACT

This invention relates to compounds of formula (1), wherein substituents are defined in the description, that inhibit farnesylation of mutant ras gene products tough inhibition of the enzyme farnesyl-protein transferase (FPTase). The invention also relates to methods of manufacturing the compounds, pharmaceutical compositions and methods of treating diseases, especially cancer, which are mediated through farnesylation of ras.

(I)

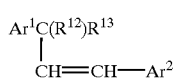

9 Claims, No Drawings

CHEMICAL COMPOUNDS

This is a 371 of International Application PCT/GB99/04308 filed Dec. 17, 1999.

This invention relates to compounds that inhibit farnesylation of mutant ras gene products through inhibition of the enzyme farnesyl-protein transferase (FPTase). The invention also relates to methods of manufacturing the compounds, pharmaceutical compositions and methods of treating diseases, especially cancer, which are mediated through farnesylation of ras.

Cancer is believed to involve alteration in expression or function of genes controlling cell growth and differentiation. Whilst not wishing to be bound by theoretical considerations the following text sets out the scientific background to ras in cancer. Ras genes are frequently mutated in tumours. Ras genes encode guanosine triphosphate (GTP) binding proteins which are believed to be involved in signal transduction, proliferation and malignant transformation. H-, K- and N-ras genes have been identified as mutant forms of ras (Barbacid M, Ann. Rev. Biochem. 1987, 56: 779–827). Post translational modification of ras protein is required for biological activity. Farnesylation of ras catalysed by FPTase is believed to be an essential step in ras processing. It occurs by transfer of the farnesyl group of farnesyl pyrophosphate (FPP) to a cysteine at the C-terminal tetrapeptide of ras in a structural motif called the CAAX box. After further post-translational modifications, including proteolytic cleavage at the cysteine residue of the CAAX box and methylation of the cysteine carboxyl, ras is able to attach to the cell membrane for relay of growth signals to the cell interior. In normal cells activated ras is believed to act in conjunction with growth factors to stimulate cell growth. In tumour cells it is believed that mutations in ras cause it to stimulate cell division even in the absence of growth factors (Travis J, Science 1993, 260: 1877–1878), possibly through being permanently in GTP activated form rather than cycled back to GDP inactivated form. Inhibition of farnesylation of mutant ras gene products will stop or reduce activation.

One class of known inhibitors of farnesyl transferase is based on farnesyl pyrophosphate analogues; see for example European patent application EP 534546 from Merck. Inhibitors of farnesyl transferase based on mimicry of the CAAX box have been reported. Reiss (1990) in Cell 62, 81–8 disclosed tetrapeptides such as CVIM (Cys-Val-Ile-Met). James (1993) in Science 260, 1937–1942 disclosed benzodiazepine based peptidomimetic compounds. Lerner (1995) in J. Biol. Chem. 270, 26802 and Eisai in International Patent Application WO 95/25086 disclosed further peptidomimetic compounds based on Cys as the first residue. Bristol-Myers Squibb in European Patent Application EP 696593 disclosed farnesyl transferase inhibitors having a 4-sulfanylpyrrolidine residue in the first position.

International Patent Application WO 97/17070 discloses a broad range of compounds which can contain an imidazole group and a methionine substituent. We have now discovered a narrow class of imidazole compounds which have improved properties.

According to one aspect of the present invention there is provided a compound of Formula (1):

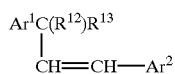

Formula (1)

wherein $Ar^1$ represents:

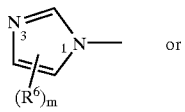

(A)

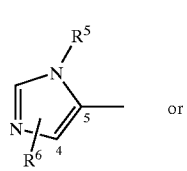

(B)

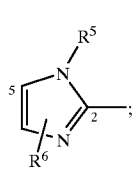

(C)

$R^5$ is hydrogen, $C_{1-4}$alkyl, phenyl$C_{1-4}$alkyl;

$R^6$ is hydrogen, $C_{1-4}$alkyl, hydroxy$C_{1-4}$alkyl, halo$C_{1-4}$alkyl, dihalo$C_{1-4}$alkyl, $C_{1-4}$alkoxy, $C_{1-4}$alkoxy$C_{1-4}$alkyl, sulfanyl$C_{1-4}$alkyl, amino$C_{1-4}$alkyl, N—($C_{1-4}$alkyl)amino$C_{1-4}$alkyl, N,N-di($C_{1-4}$alkyl)amino$C_{1-4}$alkyl or phenyl$C_{1-4}$alkyl; m is 0,1 or 2;

$R^{12}$ and $R^{13}$ are independently hydrogen or $C_{1-4}$alkyl;

$Ar^1$ is phenyl, pyridyl, pyridazinyl, pyrimidyl, pyrazinyl, thienyl, thiazolyl, furyl or oxazolyl, the ring being substituted on ring carbon atoms by $R^2$ and —$(CH_2)_n$$R^3$, wherein $Ar^2$ is attached to $Ar^1C(R^{12})R^{13}CH=CH$— by a ring carbon atom; or $Ar^1$ is pyrrolyl, pyrazolyl or imidazolyl, substituted by $R^2$ and —$(CH_2)_n$$R^3$ (the pyrrolyl, pyrazolyl or imidazolyl rings can bear a substituent on the $sp^3$ hybridised ring nitrogen or $Ar^2$ can be attached to $Ar^1(R^{12})R^{13}CH=CH$— by the $sp^3$ hybridised ring nitrogen);

$R^2$ is a group of the Formula (2):

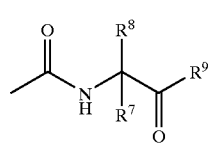

Formula (2)

wherein $R^7$ is hydrogen or $C_{1-4}$alkyl, $R^8$ is —$(CH_2)_q$—$R^{10}$ wherein q is 0–4 and $R^{10}$ is $C_{1-4}$alkylsulfanyl, $C_{1-4}$alkylsulfinyl, $C_{1-4}$alkylsulfonyl, hydroxy, $C_{1-4}$alkoxy, carbamoyl, N—$C_{1-4}$alkyl carbamoyl, N,N-(di$C_{1-4}$alkyl)carbamoyl, $C_{1-4}$alkyl, phenyl, thienyl, or $C_{1-4}$alkanoylamino, $R^9$ is hydroxy, $C_{1-6}$alkoxy, $C_{3-9}$cycloalkyloxy, heterocyclyloxy, heterocyclyl$C_{1-4}$alkoxy or —NH—$SO_2$—$R^{11}$ wherein $R^{11}$ represents, trifluoromethyl, $C_{1-4}$alkyl, phenyl, heteroaryl, aryl$C_{1-4}$alkyl or heteroaryl$C_{1-4}$alkyl;

or $R^2$ represents a lactone of Formula (3)

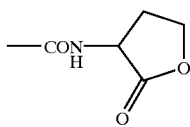

Formula (3)

the group of Formula (2) or (3) having L or D configuration at the chiral alpha carbon in the corresponding free amino acid;
n is 0, 1, or 2;
$R^3$ is phenyl or heteroaryl;
or $R^2$ is a group of the Formula (4):

Formula (4)

wherein $R^{14}$ is —$(CH_2)_q$—$R^{15}$ wherein q is 0–4 and $R^{15}$ is $C_{1-4}$alkylsulfanyl, $C_{1-4}$alkylsulfinyl, $C_{1-4}$alkylsulfonyl, hydroxy, $C_{1-4}$alkoxy, carbamoyl, N—$C_{1-4}$alkyl carbamoyl, N,N-(di$C_{1-4}$alkyl) carbamoyl, $C_{1-4}$alkyl, phenyl, thienyl, or $C_{1-4}$alkanoylamino; $R^{14}$ is of the formula —$CH_2OR^{17}$ (wherein $R^{17}$ is hydrogen, $C_{1-4}$alkyl, phenyl, heteroaryl, $C_{2-5}$alkanoyl, $C_{1-4}$alkoxymethyl, phenoxymethyl or heteroaryloxymethyl), of the formula —$COR^{18}$ or of the formula —$CH_2COR^{15}$ (wherein $R^{18}$ is $C_{1-4}$alkyl (optionally substituted by halo, cyano, $C_{2-5}$alkanoyloxy, hydroxy, $C_{1-4}$alkoxy or $C_{1-4}$alkanoyl), phenyl, phenyl$C_{1-4}$alkyl, heteroaryl, heteroaryl$C_{1-4}$alkyl, $C_{5-7}$cycloalkyl, $C_{5-7}$cycloalkyl$C_{1-3}$alkyl, 2-(phenyl)ethenyl, 2-(heteroaryl)ethenyl or N-methoxy-N-methylamino); or $R^{13}$ is morpholino$C_{1-4}$alkyl, pyrrolidin-1-yl$C_{1-4}$alkyl or piperidin-1-yl$C_{1-4}$alkyl wherein the morpholine, pyrrolidine and piperidine rings are optionally substituted by $C_{1-4}$alkyl or $C_{5-7}$cycloalkyl; or $R^{13}$ is phenyl-1-hydroxy$C_{1-4}$alkyl or heteroaryl-1-hydroxy$C_{1-4}$alkyl;
phenyl and heteroaryl rings in $R^3$, $R^5$, $R^6$, $R^{11}$ and $R^{15}$ (including $R^{17}$ and $R^{18}$) are independently optionally substituted on ring carbon atoms by up to three substituents selected from $C_{1-4}$alkyl, halogen, hydroxy, $C_{1-4}$alkoxy, $C_{1-4}$alkoxycarbonyl, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, thiol, $C_{1-4}$alkylsulfanyl, $C_{1-4}$alkylsulfinyl, $C_{1-4}$alkylsulfonyl, $C_{1-4}$alkanesulphonamido, N—($C_{1-4}$alkylsulphonyl)—N—$C_{1-4}$alkylamino, aminosulfonyl, N—($C_{1-4}$alkyl)aminosulfonyl, N,N-di($C_{1-4}$alkyl)aminosulfonyl, carbamoyl, N—($C_{1-4}$alkyl)carbamoyl, N,N-(di$C_{1-4}$alkyl) carbamoyl, carbamoyl$C_{1-4}$alkyl, N—($C_{1-4}$alkyl) carbamoyl$C_{1-4}$alkyl, N,N-(di$C_{1-4}$alkyl) carbamoyl$C_{1-4}$alkyl, hydroxy$C_{1-4}$alkyl and $C_{1-4}$alkoxy$C_{1-4}$alkyl and on ring NH groups (replacing hydrogen) by $C_{1-4}$alkyl, $C_{1-4}$alkanoyl, $C_{1-4}$alkylsulfonyl, halo$C_{1-4}$alkyl, difluoromethyl or trifluoromethyl;
or a pharmaceutically-acceptable salt, prodrug or solvate thereof In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula (1) defined above may exist in optically active or racemic forms by virtue of one or more asymmetric carbon atoms, the invention includes in its definition any such optically active or racemic form which possesses the property of inhibiting FTPase. The synthesis of optically active forms may be carried out by standard techniques of organic chemistry well known in the art, for example by synthesis from optically active starting materials or by resolution of a racemic form. Similarly, inhibitory properties against FTPase may be evaluated using the standard laboratory techniques referred to hereinafter.

The term "heterocyclyl" refers to a 5- or 6-membered monocyclic ring containing 1 to 3 heteroatoms selected from nitrogen, oxygen and sulfur.

The term "heteroaryl" refers to a 5–10 membered monocyclic heteroaryl ring containing 1 to 3 heteroatoms selected from nitrogen, oxygen and sulphur.

The ring $sp^3$ hybridised ring nitrogen in the pyrrolyl, pyrazolyl or imidazolyl rings is the ring nitrogen which can be substituted without becoming quaternised i.e. the ring >NH nitrogen.

The term "halogen" refers to fluorine, chlorine, bromine and iodine. The term "carbamoyl" refers to —$C(O)NH_2$. The term "BOC" refers to tert-butoxycarbonyl.

Examples of $C_{1-4}$alkyl include methyl, ethyl, propyl, isopropyl, sec-butyl and tert-butyl; examples of $C_{1-4}$alkoxy include methoxy, ethoxy and propoxy; examples of $C_{1-4}$alkanoyl include formyl, acetyl and propionyl; examples of $C_{1-4}$alkanoyloxy include acetyloxy and propionyloxy; examples of $C_{1-4}$alkylamino include methylamino, ethylamino, propylamino, isopropylamino, sec-butylamino and tert-butylamino; examples of di-($C_{1-4}$alkyl)amino include di-methylamino, di-ethylamino and N-ethyl-N-methylamino; examples of $C_{1-4}$alkanoylamino include acetamido and propionylamino; examples of $C_{1-4}$alkoxycarbonyl include methoxycarbonyl, ethoxycarbonyl and propoxycarbonyl; examples of $C_{1-4}$alkylsulfanyl include methylsulfanyl, ethylsulfanyl, propylsulfanyl, isopropylsulfanyl, sec-butylsulfanyl and tert-butylsulfanyl; examples of $C_{1-4}$alkylsulfinyl include methylsulfinyl, ethylsulfinyl, propylsulfinyl, isopropylsulfinyl, sec-butylsulfinyl and tert-butylsulfinyl; examples of $C_{1-4}$alkylsulfonyl include methylsulfonyl, ethylsulfonyl, propylsulfonyl, isopropylsulfonyl, sec-butylsulfonyl and tert-butylsulfonyl; examples of N—($C_{1-4}$alkyl)carbamoyl include N-methylcarbamoyl and N-ethylcarbamoyl; examples of N,N-(di$C_{1-4}$alkyl)carbamoyl include N,N-dimethylcarbamoyl and N-methyl-N-ethylcarbamoyl; examples of $C_{1-4}$alkanesulfonamido include methanesulfonamido, ethanesulphonamido and propanesulfonamido; examples of $C_{1-4}$alkylsulfonyl-N—$C_{1-4}$alkylamino include methylsulfonyl-N-methylamino, ethylsulfonyl-N-methylamino and propylsulfonyl-N-methylamino; examples of fluoro$C_{1-4}$alkyl include fluoromethyl, 2-fluoroethyl and 3-fluoropropyl; examples of difluoro$C_{1-4}$alkyl include difluoromethyl, 2,2-difluoroethyl and 3,3-difluoropropyl; examples of carbamoyl$C_{1-4}$alkyl include carbamoylmethyl, carbamoylethyl and carbamoylpropyl; examples of N—($C_{1-4}$alkyl)carbamoyl$C_{1-4}$alkyl include N-methyl-carbamoylmethyl and N-ethyl-carbamoylethyl; examples of N,N-(di$C_{1-4}$alkyl) carbamoyl$C_{1-4}$alkyl include N,N-dimethylcarbamoylethyl and N-methyl-N-ethylcarbamoylethyl; examples of hydroxyC$_{1-4}$alkyl include hydroxymethyl, hydroxyethyl, hydroxypropyl, 2-hydroxypropyl, 2-(hydroxymethyl)propyl and hydroxybutyl; examples of C$_{1-4}$alkoxyC$_{1-4}$alkyl include methoxyethyl, ethoxyethyl and methoxybutyl; examples of sulfanylC$_{1-4}$alkyl include sulfanylmethyl, sulfanylethyl, sulfanylpropyl; and examples of N—(C$_{1-4}$alkyl)aminoC$_{1-4}$alkyl include N-methyl-aminomethyl and N-ethyl-aminoethyl.

Examples of 5- or 6-membered heteroaryl ring systems include imidazole, triazole, pyrazine, pyrimidine, pyridazine, pyridine, isoxazole, oxazole, isothiazole, thiazole and thiophene.

Preferably the NH group in imidazole is unsubstituted or substituted by C$_{1-4}$alkyl. Examples of heterocyclyl rings include pyrrolidinyl, morpholinyl, piperidinyl, dihydropyridinyl and dihydropyrimidinyl.

Preferred heteroatoms are N and S, especially N. In general, attachment of heterocyclic rings to other groups is via carbon atoms.

Examples of values for $R^8$ in Formula (2) are side chains of lipophilic amino acids including such as for example methionine, phenylglycine, phenylalanine, serine, leucine, isoleucine or valine. The L configuration in the corresponding free amino acid is preferred. Examples of amino acid side chains are set out below.

| Amino Acid | Side Chain |
| --- | --- |
| methionine | —CH$_2$—CH$_2$—S—CH$_3$ |
| phenylglycine | Ph |
| phenylalanine | —CH$_2$-Ph |
| thienylalanine | —CH$_2$-thien-2-yl |
| serine | —CH$_2$OH or a C$_{1-4}$alkyl (preferably methyl) ether thereof. |
| Leucine | —CH$_2$—CHMe$_2$ |
| homoserine | —CH$_2$—CH$_2$—OH or a C$_{1-4}$alkyl (preferably methyl) ether thereof |
| N-acetyl-lysine | —CH$_2$—CH$_2$—CH$_2$—CH$_2$—NH—CO—CH$_3$ |

The lactone in Formula (3) can be formed from a group of Formula (2) when $R^9$ is OH to give a carboxyl and $R^8$ is —CH$_2$—CH$_2$—OH where $R^8$ and $R^9$ together lose a water molecule to form part of a dihydrofuran-2-one heterocyclic ring.

Preferably, phenyl and heteroaryl rings in $R^3$, $R^5$, $R^6$, $R^{11}$ and $R^{15}$ (including $R^{17}$ and $R^{18}$) are independently optionally substituted on ring carbon atoms by up to two substituents selected from C$_{1-4}$alkyl, halogen, hydroxy, C$_{1-4}$alkoxy, C$_{1-4}$alkoxycarbonyl, C$_{1-4}$alkanoyl, C$_{1-4}$alkanoyloxy, amino, C$_{1-4}$alkylamino, di(C$_{1-4}$alkyl)amino, C$_{1-4}$alkanoylamino, cyano, carboxy, C$_{1-4}$alkylsufanyl, C$_{1-4}$alkylsulfinyl, C$_{1-4}$alkylsulfonyl, C$_{1-4}$alkanesulphonamido, carbamoyl, N—(C$_{1-4}$alkyl)carbomoyl, N,N-(diC$_{1-4}$alkyl)carbamoyl and on ring NH groups (replacing hydrogen) by C$_{1-4}$alkyl or C$_{1-4}$alkanoyl.

Preferably $R^{12}$ and $R^{13}$ are independently hydrogen or methyl.

Most preferably $R^{12}$ and $R^{13}$ are hydrogen. Preferably $R^6$ is hydrogen, C$_{1-4}$alkyl, hydroxyC$_{1-4}$alkyl, aminoC$_{1-4}$alkyl, fluoroC$_{1-4}$alkyl, difluoroC$_{1-4}$alkyl, C$_{1-4}$alkoxy or C$_{1-4}$alkoxyC$_{1-4}$alkyl.

More preferably $R^6$ is hydrogen, methyl, fluoromethyl, difluoromethyl, methoxy or methoxymethyl.

Most preferably $R^6$ is hydrogen or methyl.

Preferably m is 0 or 1.

Preferably $R^5$ is hydrogen or methyl. More preferably $R^5$ is hydrogen.

In a particular aspect $Ar^1$ is 1-methylimidazol-5-yl.

Preferably $Ar^2$ is phenyl, pyridyl, pyridazinyl, pyrimidyl, pyrazinyl, thienyl, thiazolyl, or oxazolyl, the ring being substituted on ring carbon atoms by $R^2$ and —(CH$_2$)$_n$R$^3$. Most preferred is where $Ar^2$ is phenyl, pyridinyl or thienyl, the ring being substituted on ring carbon atoms by $R^2$ and —(H$_2$)$_n$R$^3$.

More preferably $Ar^2$ is phenyl, pyridinyl or thienyl, the ring being substituted on ring carbon atoms by $R^2$ and —(CH$_2$)$_n$R$^3$.

Yet more preferably $Ar^2$ is phenyl or pyridyl, the ring being substituted on ring carbon atoms by $R^2$ and —(CH$_2$)$_n$R$^3$.

Most preferably $Ar^2$ is phenyl, the ring being substituted on ring carbon atoms by $R^2$ and —(CH$_2$)$_n$R$^3$.

Preferably, when n is 0, $Ar^2$ is substituted by $R^2$ in the 4-position and —(CH$_2$)$_n$R$^3$ in the 3- or 5-position and when n is 1 or 2, $Ar^2$ is substituted by $R^2$ in the 3- or 5-position and —(CH$_2$)$_n$R$^2$ in the 4-position. The positions indicated are relative to the point of attachment of $Ar^2$ to $Ar^1$C($R^{12}$)$R^{13}$CH=CH—.

Preferably n is 0 or 2. In a particular aspect n is 0.

$R^2$ is preferably a group of formula:

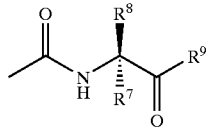

$R^7$ is preferably hydrogen or methyl, especially hydrogen. In $R^8$, q is preferably 1–4, more preferably 1 or 2, especially 2.

Within $R^8$, $R^{10}$ is preferably C$_{1-4}$alkylsulfanyl, C$_{1-4}$alkylsulfinyl, C$_{1-4}$alkylsulfonyl, hydroxy or C$_{1-4}$alkoxy. More preferably $R^{10}$ is methylsulfanyl or methylsulfonyl.

$R^9$ is preferably hydroxy, C$_{1-4}$alkoxy, C$_{3-9}$cycloalkyloxy, heterocyclyloxy or heterocyclylC$_{1-4}$alkoxy. More preferably $R^9$ is hydroxy, methoxy, propoxy, butoxy, tert-butoxy, cyclopentyloxy, piperidin-4-yloxy or morpholinoC$_{1-4}$alkyl. Most preferably, $R^9$ is methoxy, prop-2-oxy, n-butoxy, tert-butoxy or cyclopentyloxy.

Preferably $R^{11}$ in $R^9$ is phenyl.

Preferred substituents for NH groups in heterocyclic groups in $R^9$ include methyl, ethyl, acetyl, propionyl, fluoromethyl, difluoromethyl and trifluoromethyl.

More preferred substituents for NH groups in heterocyclic groups in $R^9$ include methyl and acetyl.

Preferred substituents for ring carbon atoms in phenyl or heteroaryl groups in $R^{11}$ include methyl, halo, C$_{1-4}$alkanoyl, nitro, cyano, C$_{1-4}$alkylsulfinyl, C$_{1-4}$alkylsulfonyl, carbamoyl, C$_{1-4}$alkylcarbamoyl and diC$_{1-4}$alkylcarbamoyl.

Formula (4) is preferably a group of formula:

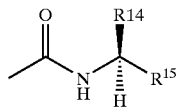

In $R^{14}$, q is preferably 1–4, more preferably 1 or 2, especially 2.

Within $R^{14}$, $R^{14}$ is preferably C$_{1-4}$alkylsulfanyl, C$_{1-4}$alkylsulfinyl, C$_{1-4}$alkylsulfonyl, hydroxy or C$_{1-4}$alkoxy. More preferably $R^{16}$ in $R^{14}$ is methylsulfanyl or methylsulfonyl. Preferably $R^{17}$ in $R^{15}$ is hydrogen or phenyl.

Most preferably $R^{17}$ in $R^{15}$ is hydrogen.

Preferably $R^{18}$ in $R^{15}$ is C$_{1-4}$alkyl, phenyl, phenylC$_{1-3}$alkyl, heteroaryl, heteroarylC$_{1-3}$alkyl or C$_{5-7}$cycloalkylC$_{1-3}$alkyl.

More preferably $R^{18}$ in $R^{15}$ is $C_{1-4}$alkyl, phenyl, phenyl$C_{1-3}$alkyl or heteroaryl.

Most preferably $R^{18}$ in $R^{15}$ is $C_{1-4}$alkyl, phenyl or benzyl.

Preferably when $R^{18}$ is $C_{1-4}$alkyl, it is optionally substituted by halo, cyano or $C_{2-6}$alkanoyloxy.

Preferably morpholino$C_{1-4}$alkyl is morpholinomethyl, pyrrolidin-1-yl$C_{1-4}$alkyl is pyrrolidin-1-ylmethyl and piperidin-1-yl$C_{1-4}$alkyl is piperidin-1-ylmethyl.

In one aspect $R^{15}$ is morpholinomethyl.

More preferably $R^{15}$ is hydroxymethyl, benzylcarbonyl, 3-(pyridyl)propionyl or morpholinomethyl.

Most preferably $R^{15}$ is hydroxymethyl or benzylcarbonyl. $R^{14}$ is —$(CH_2)_qR^{16}$ wherein q is 0–4 and $R^{16}$ is $C_{1-4}$alkylsulfanyl, $C_{1-4}$alkylsulfinyl, $C_{1-4}$alkylsulfonyl, hydroxy or $C_{1-4}$alkoxy; or $R^{15}$ is morpholinomethyl, pyrrolidin-1-ylmethyl or piperidin-1-ylmethyl; or $R^{15}$ is of the formula —$CH_2OR^{17}$ wherein $R^{17}$ is hydrogen or phenyl; or $R^{15}$ is of the formula —$COR^{18}$ or —$CH_2COR^{18}$ wherein $R^{18}$ is $C_{1-4}$alkyl, phenyl, phenyl$C_{1-3}$alkyl, heteroaryl, heteroaryl$C_{1-3}$alkyl or $C_{5-7}$cycloalkyl$C_{1-3}$alkyl; Preferably $R^3$ is phenyl, pyridyl or thiazolyl.

Most preferably $R^3$ is phenyl.

Preferred substituents for ring carbon atoms in $R^3$ include $C_{1-4}$alkyl, halo, trifluoromethyl, $C_{1-4}$alkoxy, nitro, cyano and $C_{1-4}$alkoxy $C_{1-4}$alkyl.

More preferred substituents for ring carbon atoms in $R^3$ include methyl, fluoro, chloro, trifluoromethyl, methoxy, nitro, cyano and methoxymethyl.

When $R^3$ is phenyl it is preferably mono-substituted by fluoro, chloro or cyano or di-substituted by fluoro and triflouromethyl, chloro and trifluoromethyl, fluoro and fluoro or chloro and chloro.

A preferred substituent for a ring NH group in a heteroaryl group in $R^3$ is $C_{1-4}$alkyl, particularly methyl.

When $R^3$ is phenyl it is preferably substituted in the 4-position, and when di-substituted it is preferably substituted in the 2- and 4-positions.

Preferably n is 0 or 2.

Preferably $R^7$ is hydrogen.

Preferably $R^8$ is —$(CH_2)$—$R^{10}$ is $C_{1-4}$alkylsulfonyl or $C_{1-4}$alkylsulfonyl.

Preferably $R^9$ is hydroxy, $C_{1-4}$alkoxy, $C_{3-9}$cycloalkyloxy, heterocyclyloxy or heterocyclyl$C_{1-4}$alkoxy.

A preferred compound of the invention is a compound of the Formula (I) wherein:

$Ar^1$ is of the formula (A), (B) or (C);

$R^5$ is hydrogen or methyl;

$R^6$ is hydrogen, $C_{1-4}$alkyl, fluoro$C_{1-4}$alkyl, difluoro$C_{1-4}$alkyl, $C_{1-4}$alkoxy or $C_{1-4}$alkoxy$C_{1-4}$alkyl;

m is 0 or 1;

$R^{12}$ and $R^{13}$ are independently hydrogen or methyl;

$Ar^2$ is phenyl or pyridyl, the ring being substituted on ring carbon atoms by $R^2$ and —$(CH_2)_nR^{10}$ and wherein $Ar^2$ is attached to $Ar^1C(R^{12})R^{13}CH=CH—$ by a ring carbon atom; and n is 0, 1 or 2;

$R^2$ is of the formula (2) wherein $R^7$ is hydrogen or methyl;

$R^5$ is —$(CH_2)_qR^{10}$ wherein q is 0–4 and $R^{10}$ is $C_{1-4}$alkylsulfanyl, $C_{1-4}$alkylsulfinyl, $C_{1-4}$alkylsulfonyl, hydroxy or $C_{1-4}$alkoxy;

$R^9$ is hydroxy, $C_{1-4}$alkoxy, $C_{3-9}$cycloalkyloxy, heterocycloxy or heterocyclyl$C_{1-4}$alkoxy;

or $R^2$ is of the formula (3);

$R^3$ is phenyl, pyridyl or thiazolyl; and phenyl, heteroaryl and heterocyclyl rings in $R^3$ and $R^9$ are independently optionally substituted on ring carbon atoms by one or two substituents selected from $C_{1-4}$alkyl, halo, $C_{1-4}$alkoxy, $C_{1-4}$alkanoyl, nitro, cyano, $C_{1-4}$alkylsulfinyl, $C_{1-4}$alkylsulfonyl, carbamoyl, $C_{1-4}$alkylcarbamoyl and di$C_{1-4}$alkylcarbamoyl; and optionally substituted on ring NH groups by $C_{1-4}$alkyl, $C_{1-4}$alkanoyl, fluoromethyl, difluoromethyl or trifluoromethyl;

or a pharmaceutically-acceptable salt, prodrug or solvate thereof.

A more preferred compound of the invention is a compound of the formula (I) wherein:

$Ar^1$ is of the formula (A), (B) or (C);

$R^5$ is hydrogen or methyl;

$R^6$ is hydrogen, methyl, fluoromethyl, difluoromethyl, methoxy or methoxymethyl;

m is 0 or 1;

$R^{12}$ and $R^{13}$ are independently hydrogen or methyl;

$Ar^2$ is phenyl or pyridyl; the ring being substituted on ring carbon atoms by $R^2$ and —$(CH_2)_nR^3$ and wherein $Ar^2$ is attached to $Ar^1C(R^{12})R^{13}CH=CH—$ by a ring carbon atom; and n is 0, 1 or 2;

$R^2$ is of formula (2) wherein $R^7$ is hydrogen or methyl;

$R^8$ is $(CH_2)_qR^{10}$ wherein q is 1 or 2, and $R^{10}$ is methylsulfanyl or methylsulfonyl;

$R^9$ is hydroxy, methoxy, prop-2-oxy, butoxy, tert-butoxy, cyclopentyloxy, piperidin-4-yloxy, or morpholino$C_{1-4}$alkyl; or $R^2$ is of the formula (3);

$R^3$ is phenyl optionally substituted by one or two substituents selected from $C_{1-4}$alkyl, halo, $C_{1-4}$alkoxy, nitro, cyano, $C_{1-4}$alkoxy$C_{1-4}$alkyl and trifluoromethyl;

or a pharmaceutically-acceptable salt, prodrug or solvate thereof.

An even more preferred compound of the invention is a compound of the formula (I) wherein:

$Ar^1$ is of the formula (A), (B) or (C);

$R^5$ is hydrogen or methyl;

$R^6$ is hydrogen or methyl;

m is 0 or 1;

$R^{11}$ and $R^{12}$ are hydrogen;

$Ar^2$ is phenyl; the ring being substituted on ring carbon atoms by $R^2$ and —$(CH_2)_nR^3$ and wherein $Ar^2$ is attached to $Ar^1(R^{12})R^{13}CH=CH—$ by a ring carbon atom;

and n is 0, 1 or 2;

$R^2$ is of the Formula (2) wherein $R^7$ is hydrogen;

$R^8$ is —$(CH_2)_8R^{10}$ wherein q is 2 and within Formula (2)

$R^{10}$ is methylsulfanyl or methylsulfonyl;

$R^9$ is hydroxy, methoxy, prop-2-oxy, butoxy, tert-butoxy, cyclopentyloxy, piperidin-4-yloxy, or 2-morpholinoprop-2-yl; or within Formula (4)

$R^{15}$ is of the fomula —$CH_2OR^{17}$ wherein $R^{17}$ is hydrogen; or $R^{15}$ is of the formula —$COR^{18}$ or —$CH_2COR^{15}$ wherein $R^{18}$ is $C_{1-4}$alkyl, phenyl, phenyl$C_{1-3}$alkyl or heteroaryl; or $R^{15}$ is morpholinomethyl, pyrrolidin-1-ylmethyl or piperidin-1-ylmethyl;

$R^3$ is phenyl optionally substituted by fluoro, chloro, cyano or trifluoromethyl;

or a pharmaceutically-acceptable salt, prodrug or solvate thereof.

Preferably $Ar^1C(R^{12})R^{13}—$ and $Ar^2$ are on opposite sides of the double bond (this gives the E isomeric configuration).

Particular compounds of the present invention include those compounds specifically described in the Examples; or a pharmaceutically-acceptable salt, prodrug or solvate thereof.

Compounds of Formula (1) may form salts which are within the ambit of the invention. Pharmaceutically acceptable salts are preferred although other salts may be useful in, for example, isolating or purifying compounds.

When the compound contains a basic moiety it may form pharmaceutically-acceptable salts with a variety of inorganic or organic acids, for example hydrochloric, hydrobromic, sulphuric, phosphoric, trifluoroacetic, citric or maleic acid. A suitable pharmaceutically-acceptable salt of the invention when the compound contains an acidic moiety is an alkali metal salt, for example a sodium or potassium salt, an alkaline earth metal salt, for example a calcium or magnesium salt, an ammonium salt or a salt with an organic base which affords a pharmaceutically-acceptable cation, for example a salt with methylamine, dimethylamine, trimethylamine, piperidine, morpholine or tris-(2-hydroxyethyl)amine.

Solvates, for example hydrates, are also within the ambit of the invention and may be prepared by generally known methods.

Various forms of prodrugs are well known in the art. For examples of such prodrugs derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

Examples of pro-drugs include in vivo hydrolysable esters of a compound of the Formula I. Suitable pharmaceutically-acceptable esters for carboxy include $C_{1-4}$alkyl esters, $C_{5-8}$cycloalkyl esters, cyclic amine esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl wherein alkyl, cycloalkyl and cyclicamino groups are optionally substituted by, for example, phenyl, heterocyclcyl, alkyl, amino, alkylamino, dialkylamino, hydroxy, alkoxy, aryloxy or benzyloxy, and may be formed at any carboxy group in the compounds of this invention.

According to another aspect of the invention there is provided a pharmaceutical composition comprising a compound as defined in Formula (1) or an individual compound listed above together with a pharmaceutically-acceptable diluent or carrier. A preferred pharmaceutical composition is in the form of a tablet.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30$\mu$ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (1) will naturally vary according to the nature and severity of the conditions, the age and sex of the animal or patient and the route of administration, according to well known principles of medicine. As mentioned above, compounds of the Formula (1) are useful in treating diseases or medical conditions which are due alone or in part to the effects of farnesylation of ras.

In using a compound of the Formula (1) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

Compounds of this invention may be useful in combination with known anti-cancer and cytotoxic agents. If formulated as a fixed dose such combination products employ the compounds of this invention within the dosage range described herein and the other pharmaceutically active agent within its approved dosage range. Sequential use is contemplated when a combination formulation is inappropriate.

According to another aspect of the invention there is provided a compound of Formula (1) or a pharmaceutically-acceptable salt thereof, for use as a medicament.

According to another aspect of the invention there is provided a compound of Formula (1) or a pharmaceutically-acceptable salt thereof, for use in preparation of a medicament for treatment of a disease mediated through farnesylation of ras.

According to another aspect of the present invention there is provided a method of treating ras mediated diseases, especially cancer, by administering an effective amount of a compound of Formula (1) or a pharmaceutically-acceptable salt thereof, to a mammal in need of such treatment.

Diseases or medical conditions may be mediated alone or in part by farnesylated ras. A particular disease of interest is cancer. Specific cancers of interest include:

carcinoma, including that of the bladder, breast, colon, kidney, liver, lung, ovary, pancreas, stomach, cervix, thyroid and skin;

hematopoietic tumors of lymphoid lineage, including acute lymphocytic leukemia, B-cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma, seminoma, tetratocarcinoma, neuroblastoma and glioma.

The compounds of Formula (1) are especially useful in treatment of tumors having a high incidence of ras mutation, such as colon, lung, and pancreatic tumors. By the administration of a composition having one (or a combination) of the compounds of this invention, development of tumors in a mammalian host is reduced.

Compounds of Formula (1) may also be useful in the treatment of diseases other than cancer that may be associated with signal transduction pathways operating through Ras, e.g., neuro-fibromatosis.

Compounds of Formula (1) may also be useful in the treatment of diseases associated with CAAX-containing proteins other than Ras (e.g., nuclear lamins and transducin) that are also post-translationally modified by the enzyme farnesyl protein transferase.

Although the compounds of the Formula (1) are primarily of value as therapeutic agents for use in warm-blooded animals (including man), they are also useful whenever it is required to inhibit the effects of activation of ras by farnesylation. Thus, they are useful as pharmacological standards for use in the development of new biological tests and in the search for new pharmacological agents.

In another aspect the present invention provides a process for preparing a compound of the Formula (1) or a pharmaceutically-acceptable salt prodrug or solvate thereof which process comprises:
deprotecting a compound of the formula (5)

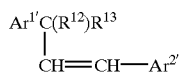

(5)

wherein $Ar^{1'}$ is $Ar^1$ or protected $Ar^1$ and $Ar^{2'}$ is $Ar^2$ or protected $Ar^2$ and $R^{12}$ and $R^{13}$ are as hereinabove defined; wherein at least one protecting group is present; and thereafter if necessary:

(i) forming a pharmaceutically-acceptable salt,
(ii) forming a prodrug,
(iii) forming a solvate.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain $C_{1-12}$alkyl groups (for example isopropyl, t-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); phenyl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and t-butyldimethylsilyl); tri(lower alkyl)silyl lower alkyl groups (for example trimethylsilylethyl); and $C_{1-6}$alkenyl groups (for example allyl and vinylethyl).

Methods particularly appropriate for the removal of carboxy protecting groups include for example acid-, base-, metal- or enzymically-catalysed hydrolysis.

Examples of hydroxy protecting groups include lower alkyl groups (for example t-butyl), lower alkenyl groups (for example allyl); lower alkanoyl groups (for example acetyl); lower alkoxycarbonyl groups (for example t-butoxycarbonyl); lower alkenyloxycarbonyl groups (for example allyloxycarbonyl); phenyl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, t-butyldimethylsilyl) and phenyl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example t-butoxycarbonyl); lower alkenyloxycarbonyl (for example allyloxycarbonyl); phenyl lower alkoxycarbonyl groups (for example benzyloxycarbonyl, p-methoxybenzyloxycarbonyl, o-nitrobenzyloxycarbonyl, p-nitrobenzyloxycarbonyl; trialkylsilyl (for example trimethylsilyl and t-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

Compounds of the formula (1) and (5) can be formed by:
(i) reacting a compound of the formula (6) with a compound of the formula (7):

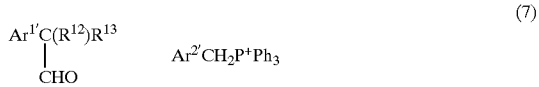

(7)

or (ii) converting one value of $R^9$ in $R^2$ into another value of $R^9$;
or (iii), where the compound of formula (I) includes alternatives of formula (2) and (3), reacting a compound in which $R^2$ in $Ar^{2'}$ is carboxy with a compound of the formula (8):

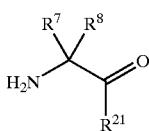

(7)

or (iv), where the compound of formula (I) includes alternative of formula (4), reacting a compound in which $R^2$ in $Ar^2$ is carboxy with a compound of formula (8a).

or (v) when $Ar^{1'}$ is of the formula (B) or (C) (optionally protected), reacting a compound of the formula (9) or (9a) with a compound of formula (10):

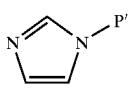

(9)

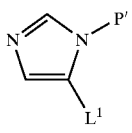

(9a)

(10)

wherein p, $Ar^{1'}$, $Ar^{2'}$, $Ar^{3'}$ $R^7$ and $R^8$ are as hereinabove defined, $R^{21}$ is $R^9$ or protected $R^9$, $L^1$ and $L^2$ are leaving groups and P' is an amino-protecting group or $R^5$ providing it is not hydrogen; and thereafter if necessary:

(i) removing any protecting groups;

(ii) forming a pharmaceutically-acceptable salt, prodrug or solvate thereof.

The reaction between compounds of the formula (6) and (7) is conveniently carried out under conditions know for the Wittig reaction.

Suitable Wittig reaction conditions include using a polar aprotic organic solvent such as THF or methylene chloride in the presence of a crown ether and an alkali metal carbonate, such as potassium carbonate, preferably at −10° C. to ambient temperature. C18 HPLC may be used to separate E and Z isomers if desired.

The Wittig reaction can be used to prepare a compound wherein $R^2$ in $Ar^{2'}$ is an alkoxycarbonyl group which may be hydrolysed to a carboxy group. If $Ar^{1'}$ is of the formula (A), and the latter route is chosen and basic conditions are used, the E and Z isomers produced by the Wittig reaction are generally not separated if the E isomer is wanted, because the base-hydrolysis step causes isomerisation of the Z isomer to the E isomer.

A compound of the formula (6) is generally prepared by reducing the corresponding ester to the aldehyde. A suitable reducing agent is for example DIBAL which is used in an inert non-polar solvent such as diethyl ether at low temperature, for example in the range −78° C. to 0° C. Other suitable reducing agents are known in the art.

Alternatively, the ester could be reduced to the corresponding alcohol with a reducing agent such as lithium aluminium hydride or sodium borohydride and the alcohol oxidised to the aldehyde with an oxidising agent such as pyridinium chlorochromate.

The ester used to form a compound of the formula (6) can be prepared by introducing Are into a compound of the formula $L^4CH_2COOR$, wherein $L^4$ is leaving group such as bromo, in the presence of a base such as sodium hydride, sodium hydroxide or potassium carbonate.

A compound of the formula (7) may be known in the art (for example see International Patent Application publication no. WO 98/32741) or may be prepared by reacting a compound of the formula $Ar^{2'}CH_2Br$ with triphenylphosphine.

A compound of the formula $Ar^{2'}CH_2Br$ may be formed by brominating a compound of the formula $Ar^{2'}CH_3$ with a suitable brominating agent such as N-bromosuccinimide.

A compound of the formula $Ar^{2'}CH_3$ wherein the $Ar^{2'}$ group is substituted by $R^2$ and $-(CH_2)_nR^3$ group may be prepared from a compound of the formula $Ar^{2'}CH_3$ wherein the $Ar^{2'}$ group is substituted by $-(CH_2)_nR^3$ and $-COOH'$ using methods described above for the conversion of $-COOH$ to $R^2$. This latter $Ar^{2'}CH_3$ compound could be prepared from a compound of the formula $Ar^{2'}CH_3$ wherein the $Ar^{2'}$ group is substituted by a protected carboxy group ($-COOP^2$) and a leaving group ($L^3$). When n is 0, the $CH_3Ar^{2'}(-COOP_2)-L^3$ compound is conveniently reacted with aryl (or heteroaryl) boronic acid in the presence of a palladium catalyst such as palladium tetrakis (triphenylphosphine) palladium (0) under conditions known for the Suzuki reaction (Synth. Commun. 11, 513 (1981)). An aprotic organic solvent such as dimethyl ether (DME), toluene, dimethylsulphoxide (DMSO) or THF is generally used and a base such as sodium bicarbonate, sodium carbonate and sometimes sodium hydroxide. A fluoride such as caesium fluoride could be used instead of the base (J. Org. Chem. 1994, 59, 6095–6097). Preferably $L^3$ is bromo or triflate.

When n is 1, the $CH_3Ar^{2'}(-COOP^2)-L^3$ compound wherein $L^3$ is bromo or chloro, is conveniently reacted with a benzyl (or heteroarylmethyl) zinc chloride or a benzyl (or heteroarylmethyl)-magnesium bromide in the presence of a nickel or palladium catalyst, such as bis(triphenylphosphine) palladium (II) chloride or $Pd_2(dba)_3$, in an inert organic solvent such as tetrahydrofuran (THF). For example see the conditions used for the 'Negishi' reaction (J. Org. Chem. 42 (10), 1821–1822, 1977).

When n is 2, the $CH_3Ar^{2'}(-COOP^2)-L^3$ compound is conveniently reacted with a styrene under conditions known for the Heck reaction. Briefly this involves an inorganic or organic base such as triethylamine, a palladium catalyst such as bis (o-tolylphosphine)palladium (II) chloride in water. (Acc. Chem. Res. 12, 146–151 (1979), J. Organometallic Chem. 486, 259–262 (1995)).

The resulting alkene can then be reduced using standard methods known in the art, for example, catalytic hydrogenation.

Alternatively the alkyne could be formed by reacting a $CH_3Ar^{2'}(-COOP_2)-L^3$ compound, wherein $L^3$ is triflate or bromo, with a phenyl acetylene in the presence of an organic base such as triethylamine and a palladium catalyst such as palladium tetrakis (triphenylphosphine). For example see the conditions used for the Sonogashira reaction (J. Org. Chem. 1993,58, 6614–6619).

The resultant alkyne can be reduced using standard methods known in the art, for example, catalytic hydrogenation.

The carboxy-protecting group may then be removed.

A compound of the formula (1) in which $R^9$ in $R^2$ is alkoxy can conveniently be hydrolysed to another compound of the formula (1) in which $R^9$ is hydroxy using standard methods known in the art. For example, the alkoxy group could be subjected to acid or base hydrolysis with, for example, in the case of base hydrolysis, aqueous sodium hydroxide solution in an organic solvent such as an alcohol in a temperature range of ambient temperature to 60° C. When $R^9$ is a hydroxy group the carboxy group in a compound of the formula (1) can be converted to an acylsulphonamide by reacting the carboxy group with the appropriate sulphonamido group in the presence of an organic base such as triethylamine or dimethylaminopyridine, in an inert organic solvent such as dimethylformamide (DMF), in temperature range of −20° C. to ambient temperature.

The reaction between a compound in which $R^2$ in $Ar^{2'}$ is carboxy and a compound of the formula (8) and (8a) is generally carried out in the presence of a reagent that converts the carboxy group into a reactive ester, for example a carbodiimide such as 1-(3-dimethylaminopropyl)-3-ethylcarbodiimide (EDC) or pentafluorophenyl, and in the presence of an organic base such as N-methylmorpholine. The reaction is usually carried out in the temperature range of −20° C. to ambient temperature. The reagents, 1-hydroxybenzotriazole and dimethylaminopyridine (DMAP), are often added to assist the reaction (see Chem. Ber. 103, 788, 2024 (1970), J. Am. Chem. Soc. 93, 6318 (1971), Helv. Chim. Acta. 56, 717, (1973)). Suitable solvents include DMF and dichloromethane.

For examples of suitable conditions for amide bond forming reactions see International Patent Application No. WO 98/07692.

A compound of the formula (1) in which $R^2$ in $Ar^{2'}$ is carboxy can be prepared by reacting a compound of the formula (6) with a compound of the formula (7), or a compound of the formula (9) or (9a) with a compound of the formula (10) wherein $R^2$ in $Ar^{2'}$ is protected carboxy and subsequently removing the carboxy-protecting group.

A compound of the formula (8a) wherein $R^{22}$ is of the formula —$COR^{18}$ can be formed via the intermediate $NH_2CH(R^{21})CON(OMe)Me$ which itself is formed by reacting together $NH_2CH(R^{21})COOH$ with N,O-dimethylhydroxylamine under standard amide bond forming conditions. A compound of the formula $NH_2CH(R^{21})CON(OMe)Me$ is then conveniently reacted with a Gringard reagent (such as $PhCH_2MgCl$) to form a compound of the formula (8).

Alternatively, when $R^{18}$ contains an alkyl chain linked to the carbonyl group, a compound of the formula $NH_2CH(R^{21})CON(OMe)Me$ can be converted to the corresponding dimethylphosphono compound $(NH_2CH(R^{21})COP(O)(OMe)_2)$ by reacting the former compound with dimethylmethylphosphonate in the presence of a strong base such as n-butyl lithium. A compound of the formula (8) can be formed by reacting the dimethylphosphono compound with the appropriate aldehyde or ketone under conditions known for the Wittig or Emmons-Horner reactions.

A compound of the formula (8) wherein $R^{22}$ is morpholinomethyl, pyrrolidin-1-ylmethyl or piperidin-1-ylmethyl is conveniently prepared by reacting $NH_2CH(R^{21})COOH$ with the appropriate heterocyclic ring under standard amide bond forming conditions to form a compound of the formula (8), wherein $R^{15}$ is heterocyclylcarbonyl, and subsequently reducing the carbonyl group to a methyl group with a reducing agent such as lithium aluminium hydride.

A compound of the formula $NH_2CH(R^{21})COOH$ can be extended by one carbon length to produce a compound of the formula $NH_2CH(R^{21})CH_2COOH$ using the Arndt-Eistert homologation method. For example by converting the carboxy group to an acid chloride, converting the latter to the diazoketone and hydrolysing this to the carboxylic acid. This homologation method could be used to produce subsequent homologues. A compound of the formula $NH_2CH(R^{21})CH_2COOH$ and homologues may be used to prepare a compound of the formula $NH_2CH(R^{21})R^{22}$ wherein $R^{22}$ is of the formula —$CH_2COR^{15}$, morpholino $C_{1-4}$alkyl, pyrrolidin-1-yl$C_{1-4}$alkyl or piperidin-1-yl$C_{1-4}$alkyl.

An anion of the formula (9) is conveniently formed with a strong base, such as n-butyl lithium. This generally forms an anion at the 2-position of the imidazole compound. The anion formation is generally carried out at low temperature e.g. −78° C., in an inert or organic solvent such as diethyl ether.

The anion (usually the lithium anion) of a compound of the formula (9) is normally converted to an organozinc reagent in the presence of lithium chloride, zinc iodide and copper (I) cyanide and this complex is reacted with a compound of the formula (10) in an inert organic solvent such as tetrahydrofuran in a temperature range of −78° C. to ambient temperature (see the review of organozinc reagents by Paul Knochel and Robert D Singer in Chem. Rev. 1993, 93, 2117–2188).

The anion of a compound of the formula (9a) is conveniently formed as a Grignard reagent by reacting the latter compound with an alkyl magnesium bromide in an ether at low temperature. The resulting Grignard reagent is typically reacted with a compound of the formula (10) in the presence of copper (I) cyanide and lithium chloride, allowing the temperature to rise from −78° C. to ambient temperature. Preferably $L^1$ in the compound of the formula (9a) is halo, for example iodo or bromo.

Preferably $L^2$ in the compound of the formula (10) is halo, for example bromo.

A compound of the formula (10) may be prepared by brominating the corresponding hydroxy compound with a brominating agent such as tetrabromomethane/triphenylphosphine in a suitable solvent such as dichloromethane. The hydroxy compound is typically prepared by reacting a compound of the formula (7) and glycoaldehyde under conditions known for the Wittig reaction such as those described above for the reaction between compounds of the formulae (6) and (7).

The order in which the various groups are introduced can be varied depending upon the nature of the desired final product. In general, the preferred last step is the formation or modification of $R^2$ in $Ar^{2'}$. For example, when $R^9$ is hydroxy, the hydrolysis of the compound wherein $R^9$ is alkoxy, or when $R^9$ is other than hydroxy, the conversion of a carboxy group to $R^2$ using the amide bond-forming conditions described above.

When $Ar^{1'}$ of the formula (A), it is preferable to form the alkene which contains a protected carboxy group later to be converted to $R^2$, by reacting together compounds of the formulae (6) and (7).

When $Ar^{2'}$ is of the formula (B) or (C) the alkene which contains a protected carboxy group later to be converted to $R^2$, is preferably formed by reacting together a compound of the formula $Ar^{2'}CH_2P^+Ph_3Br$ (wherein $Ar^{2'}$ is substituted by —$COOP^2$ in place of $R^2$) and glycoaldehyde, converting the resultant hydroxy compound to a compound of the formula (9) (wherein $Ar^{2'}$ is substituted by —$COOP^2$ in place of $R^2$) and reacting the latter compound with a compound of the formula (8) or (8a).

Optionally substituents in a compound of the formula (1) and (5) or intermediates in their preparation may be converted into other optional substituents. For example an alkylthio group may be oxidised to an alkylsulphinyl or alkysulphonyl group, a nitro group reduced to an amino group, a hydroxy group alkylated to a methoxy group, or a bromo group converted to an alkylthio group.

Various substituents may be introduced into compounds of the formulae (1) and (5) and intermediates in this preparation, when appropriate, using standard methods known in the art. For example, an acyl group or alkyl group may be introduced into an activated benzene ring using Friedel-Crafts reactions, a formyl group by formylation with titanium tetrachloride and dichloromethyl ethyl ester, a nitro group by nitration with concentrated nitric acid concentrated sulphuric acid and bromination with bromine or tetra(n-butyl)ammonium tribromide.

It will be appreciated that, in certain steps in the reaction sequence to compounds of the formula (1), it will be necessary to protect certain functional groups in intermediates in order to prevent side reactions. Deprotection may be carried out at a convenient stage in the reaction sequence once protection is no longer required.

Biological activity was tested as follows:
(i) In-vitro Assay

The following stock solutions were used and the assays were conducted in 96 well plates: TRIS Buffer (500 mM TRIS, 5 mM $MgCl_2.6H_2O$, pH=8.0); Farnesyl pyrophosphate (6.4 mg/ml); Aprotinin (1.9 mg/ml); Ki-ras (0.5 mg/ml, stored at −80° C.); Acid ethanol (850 ml absolute ethanol+150 ml concentrated HCl).

Farnesyl protein transferase (FPT) was partially purified from human placenta by ammonium sulphate fractionation followed by a single Q-Sepharose™ (Pharmacia, Inc) anion exchange chromatography essentially as described by Ray and Lopez-Belmonte (Ray K P and Lopez-Belmonte J (1992) Biochemical Society Transactions 20 494–497). The substrate for FPT was Kras (CVIM C-terminal sequence). The cDNA for oncogenic val 12 variant of human c-Ki-ras-2 4B was obtained from the plasmid pSW11-1 (ATCC). This was then subcloned into the polylinker of a suitable expression vector e.g. pIC147. The Kras was obtained after expression in the $E.\ coli$ strain, BL21. The expression and purification of c-KI-ras-2 4B and the val12 variant in $E.\ coli$ has also been reported by Lowe et al (Lowe P N et al. J. Biol. Chem. (1991) 266 1672–1678). The farnesyl protein transferase enzyme preparation was stored at −80° C.

The farnesyl transferase solution for the assay contained the following: dithiothreitol (DTT)(0.6 ml of 7.7 mg/ml), TRIS buffer (0.6 ml), aprotinin (0.48 ml), distilled water (1.2 ml), farnesyl transferase (0.6 ml of the crude enzyme preparation prepared as described above), zinc chloride (12 μl of 5 mM). This was left at ambienttemperature for 30 minutes. After this incubation 60 μl Ki-ras solution was added and the whole left to incubate for a further 60 minutes prior to use in the assay.

Assays were performed in 96 well plates as follows: 10 μl of test compound solution was added to each well. Then 30 μl farnesyl transferase solution (above) was added and the reaction started by addition of 10 μl radiolabelled farnesyl pyrophosphate solution. After 20 minutes at 37° C. the reaction was stopped with 100 μl acid ethanol (as described in Pompliano D L et al (1992) 31 3800–3807). The plate was then kept for 1 hour at 4° C. Precipitated protein was then collected onto glass fibre filter mats (B) using a Tomtec™ cell harvester and tritiated label was measured in a Wallac™ 1204 Betaplate scintillation counter. Test compounds were added at appropriate concentrations in DMSO (3% final concentration in test and vehicle control).

(ii) Intracellular Farnesylation Assay

HER313A cells (Grand et al, 1987 Oncogene 3, 305–314) were routinely cultured in Dulbecos Modified Essential Medium (DMEM) plus 10% foetal calf serum (FCS). For the assay HER313A cells were seeded at 200,000 cells/well in a volume of 2.5 ml in a 6 well tissue culture plate. After an overnight incubation at 37° C. in 10% $CO_2$ the medium was removed and replaced with methionine-free minimal essential medium (MEM) and the cells incubated as above for 2 hours. After this time the medium was removed and replaced by methionine-free MEM (1 ml) and test compound (1–3 μl). The plates were then incubated for a further 2 hours as described above and then 30 μCi of $^{35}S$-methionine added to each well. The plate was then incubated overnight as described above. The medium was then removed and the cells were lysed with lysis buffer (1 ml) (composed of 1000 ml phosphate buffered saline, 10 ml trition X-100, 5 g sodium deoxycholate, 1 g sodium dodecylsulphate) containing aprotinin (10 μl/ml), the plate scrapped and then left for 10 minutes at 4° C. The lysate was then clarified by centrifugation. To 0.8 ml of the clarified lysate 80 μl of Y13-259 pan-Ras antibody (isolated from the hybridoma—American Tissue Culture Collection Accession Number CRL-1742) (final concentration approximately 1 μ/ml, the exact working concentration was optimised for each batch of antibody isolated) and protein G beads (30 μof 0.5 μg/ml) were added and the mixture incubated overnight with constant agitation. The pellet was then collected by centrifugation, washed and separated by SDS PAGE using a 15% gel. Radioactive bands were detected using a phosphorimager system.

(iii) Morphology and Proliferation Assay

MIA PaCa 2 cells (American Tissue Culture Collection Accession Number: CRL-1420) were routinely cultured in Dulbecos Modified Essential Medium (DMEM) plus 10% FCS in a 162 $cm^2$ tissue culture flask. For the assay the cells were seeded at 16,000 cells/well, in 12 well plates, in DMEM containing 5% charcoal dextran treated stripped FCS (1 ml) (obtained from Pierce and Warriner). The cells were then incubated overnight at 37° C. in 10% $CO_2$. Test compound was then added (10 μl) and the cells incubated for 6 days as described above. On days 1, 2, 3 and 6 the cells were monitored for signs of morphological change and toxicity. On day 6 the cells were removed from the plate using trypsin/EDTA and counted to determine the proliferation rate.

Although the pharmacological properties of the compounds of the Formula (1) vary with structural change as expected, in general compounds of the Formula (1) possess an $IC_{50}$ in test (i) above in the range, for example, 0.00005 to 50 μM in test (i). Thus by way of example the compound of Example 29 herein has an $IC_{50}$ of approximately 0.0004 μM in test unacceptable toxicity was observed at the effective dose for compounds tested of the present invention.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at ambient temperature, that is in the range 18–25° C. and under an atmosphere of an inert gas such as nitrogen or argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) C18 reverse phase silica separation;

(iv) yields are given for illustration only and are not necessarily the maximum attainable;

(v) the end-products of the Formula (1) have satisfactory microanalyses and their structures were confirmed by nuclear magnetic resonance (NMR) and mass spectral techniques; chemical shift values were measured on the delta scale; the following abbreviations have been used: s, singlet; d, doublet; t or tr, triplet; m, multiplet; br, broad;

(vi) intermediates were not generally fully characterised and purity was assessed by thin layer chromatographic, HPLC, infra-red (IR) or NMR analysis;

(vii) melting points are uncorrected and were determined using a Mettler SP62 automatic melting point apparatus or an oil-bath apparatus; melting points for the end-products of the Formula (1) were determined after crystallisation from a conventional organic solvent such as ethanol, methanol, acetone, ether or hexane, alone or in admixture; and (viii) the following abbreviations have been used:

| DMAP | 4-dimethylaminopyridine |
| DMF | dimethylformamide |
| EDC | 1-(3-dimethylaminopropyl)-3-ethyl-carbodiimide |
| HOBT | 1-hydroxybenzotriazole |
| MCPBA | m-chloroperoxybenzoic acid |
| TFA | trifluoroacetic acid |
| THF | tetrahydrofuran |

EXAMPLE 1

(2S)-2-{4-[(E)-3-Imidazol-1-yl)prop-1-en-1-yl]-2-(4-fluorophenyl)benzamido}-4-methylsulfanylbutyric Acid A solution of tert-butyl (2S)-2-{4-[(E)-3-(imidazol-1-yl)prop-1-en-1-yl]-2-(4-fluorophenyl)benzamido}-4-methylsulfanylbutyrate (0.2 g; 0.4 mmol) in dichloromethane (2 ml) was treated at 0° C. with TFA (2 ml). The mixture was allowed to warm to ambient temperature and stirred for 1 hour. After evaporation of the solvent, the residue was taken up with distilled water (5 ml); the pH was adjusted to 6 with $NH_4OH$ and the solution was purified on reverse phase silica eluting with methanol/ammonium carbonate buffer (2 g/l; pH 7) (40/60) to give the title compound after freeze-drying. Yield: 40%

$^1$H NMR (DMSO+$CF_3$COOD, 400 MHz) δ: 1.8–2 (2H, m); 2 (3H, s); 2.15–2.4 (2H, m); 4.32 (1H, m); 5.05 (2H, m); 6.6–6.85 (2H, m); 7.20 (2H, m); 7.4–7.6 (5H, m); 7.7–7.85 (2H, m); 9.21 (1H, s).

| Anal. Calculated for $C_{24}H_{24}N_3O_3SF$ 1.11 $H_2O$ | C 60.90 | H 5.58 | N 8.88 | S 6.77 |
| Found | C 60.80 | H 5.32 | N 8.83 | S 6.37 |

MS (ESI) m/z: 454 ($MH^+$).

EXAMPLE 2 tert-Butyl (2S)-2-{4-[(E)-3-(Imidazal-1-yl)prop-1-en-1-yl]-2-(4-fluorophenyl)benzamido}-4-methylsulfanylbutyrate A solution of 4-[(E)-3-(imidazol-1-yl)prop-1-en-1-yl]-2-(4-fluorophenyl)benzoic acid (0.322 g; 1 mmol), EDC (0.230 g; 1.2 mmol), DMP (0.134 mg; 1.1 mmol), HOBT (162 mg; 1.2 mmol) and tert-butyl (2S)-2-amino-4-methylsulfanylbutanoate (L-methionine t-butyl ester) (0.3 g; 1.5 mmol) in dichloromethane (20 ml) was stirred at ambient temperature for 5 hours. The organic phase was washed with 5% sodium hydrogen carbonate solution and evaporated to dryness; the residue was purified by flash chromatography eluting with dichloromethane/ethanol (98/2) to give the title compound as a foam. Yield: 60%

$^1$H NMR ($CDCl_3$, 400 MHz) δ: 1.41 (9H, m); 1.7–2 (2H, m); 2 (3H, s); 2.18 (2H, m); 4.54 (1H, m); 4.75 (2H, m); 6 (1H, d); 6.3–6.55 (2H, m); 6.96 (1H, s); 7.05–7.70 (9H, m).

| Anal. Calculated for $C_{28}H_{32}FN_3O_3S$ | C 65.99 | H 6.33 | N 8.24 | S 6.29 |
| Found | C 65.81 | H 6.78 | N 8.21 | S 6.07 |

MS (ESI) m/z: 510 ($MH^+$).

The starting material was prepared as follows:

A solution of DIBAL in hexane (440 ml) was added dropwise at –70° C. under argon atmosphere to a suspension of ethyl 2-(imidazol-1-yl)acetate (27.13 g; 0.176 mole) in ether (1.2 l). The mixture was stirred at –70° C. for 2 hours 30 minutes. Methanol (100 ml) and distilled water (8 ml) were then added at –70° C. and the mixture was allowed to warm to ambient temperature and stirred for 2 hours. The resulting precipitate was filtered, washed with dichloromethane/methanol (2×400 ml) and the filtrate was evaporated and purified by flash chromatography eluting with a gradient 10–25% methanol/dichloromethane to give 2-(imidazol-1-yl)acetaldehyde which was isolated as the hemiacetal 2-(imidazol-1-yl)-1-methoxyethanol. Yield: 68%

$^1$H NMR ($CDCl_3$, 400 MHz) δ: 3.48 (3H, s); 4.02 (2H, d); 6.9–7.5 (3H, m).

A solution of 2-(imidazol-1-yl)acetaldehyde (2.6 g; 0.018 mmol), 3-(4-fluorophenyl)-4-methoxycarbonylbenzyl triphenylphosphonium bromide (5.4 g; 0.09 mmol), potassium carbonate (1.38 g; 0.01 mmol) and 18 crown-6 (0.1 g; 0.37 mmol) in THF (150 ml) was stirred under argon atmosphere at ambient temperature overnight. After filtration of the insoluble material and evaporation to dryness, the residue was purified by flash chromatography eluting with a mixture of dichloromethane/ethanol (98/2) to give methyl 4-[3-(imidazol-1-yl)prop-1-en-1-yl]-2-(4-fluorophenyl)benzoate as a mixture of E and Z isomers. Yield: 93%.

A solution of methyl 4-[3-(imidazol-1-yl)prop-1-en-1-yl]-2-(4-fluorophenyl)benzoate (B and Z isomers) (1.9 g; 5.6 mmol) and 2N aqueous sodium hydroxide solution (8.5 ml; 17 mmol) in methanol (100 ml) was refluxed for 9 hours. After evaporation and acidification with 12N HCl (1.5 ml), the resulting solid was washed with distilled water and ether, taken up in dichloromethane/methanol (99/1) to give 4-[(E)-3-(imidazol-1-yl)prop-1-en-1-yl]-2-(4-fluorophenyl) benzoic acid (E isomer) after evaporation as a foam. Yield: 89%

$^1$H NMR (DMSO+$CF_3$COOD, 400 MHz) δ: 5.06 (2H, d); 6.7–7.85 (2H, m); 7.1–7.9 (9H, m); 9.22 (1H, s).

EXAMPLE 3

Methyl (2S)-2-{4-[(E)-3-(Imidazol-1-yl)prop-1-en-1-yl]-2-(4-fluorophenyl)benzamido}-4-methylsulfanylbutyrate The title compound was prepared using the same method as described for Example 2, but using the L-methionine methyl ester in place of the L-methionine tert-butyl ester. Yield: 83%

$^1$H NMR ($CDCl_3$, 400 MHz) δ: 1.75–2.05 (2H, m); 2.03 (3H, s); 2.15–2.25 (2H, m); 3.68 (3H, s); 4.65–4.72 (1H, m);

4.74 (2H, m); 6 (1H, d); 6.35–6.43 (1H, m); 6.52 (1H, d); 6.96 (1H, s); 7.1–7.7(9H, m).

| Anal. Calculated for $C_{25}H_{26}FN_3O_3S$ | C 64.22 | H 5.61 | N 8.99 | S 6.86 |
|---|---|---|---|---|
| Found | C 63.87 | H 5.73 | N 8.80 | S 6.58 |

MS (ESI) m/z: 4680 (MH⁺).

EXAMPLE 4 tert-Butyl (2S)-2-{4-[(E)-3-(Imidazol-1-yl)prop-1-en-1-yl]-2-(4-fluorophenyl)benzamido}-4-methylsulfonylbutyrate MCPBA (0.89 g; 3.1 mmol) was added to a solution of tert-butyl (2S)-2-{4-[(E)-3-(imidazol-1-yl)prop-1-en-1-yl]-2-(4-fluorophenyl)benzamido}-4-methylsulfanylbutyrate (0.64 g; 1.25 mmol) in methylene chloride (15 ml) at 0° C. After stirring at ambient temperature for 2 hours, the solution was washed with 1M $Na_2S_2O_3$, and 5% sodium hydrogen carbonate solution. The organic layer was evaporated and the residue was purified by flash chromatography using a gradient of ethanol in dichloromethane (2%–4%) to give after evaporation of the appropriate fractions and trituration in ether, the expected compound as a solid. Yield: 51%

M.P.: 100–104° C.; ¹H NMR (CDCl₃, 400 MHz) δ: 1.42 (9H, s); 1.9–2.4 (2H, m); 2.65–2.95 (2H, m); 2.84 (3H, s); 4.5 (1H, m); 4.74 (2H, d); 6.08 (1H, d); 6.3–6.45 (2H, m); 6.96 (1H, s); 7.1–7.7 (9H, m).

| Anal. Calculated for $C_{28}H_{32}FN_3O_5S$, 0.16 Et₂O, 0.25 H₂O | C 61.65 | H 6.16 | N 7.53 | S 6.97 |
|---|---|---|---|---|
| Found | C 61.27 | H 6.13 | N 7.59 | S 6.13 |

MS (ESI) m/z: 542 (MH⁺).

EXAMPLE 5

(2S)-2-{4-[(E)-3-(Imidazol-1-yl)prop-1-en-1-yl]-2-(4-fluorophenyl)benzamido}-4-methylsulfonylbutyric Acid The title compound was prepared from Example 4 using similar methodology to that of Example 1. Yield: 45%.

¹H NMR (DMSOd₆+CF₃COOD, 400 MHz) δ: 1.9–2.25 (2H, m); 2.8–3.15 (2H, m); 2.96 (3H, s); 4.35 (1H, m); 5.06 (2H, d); 6.6–6.8 (2H, m); 7.2 (2H, m); 7.4–7.6 (5H, m); 7.74 (1H, d); 7.80 (1H, d); 9.21 (1H, s).

| Anal. Calculated for $C_{24}H_{24}FN_3O_5S$, 1.6 H₂O | C 56.04 | H 5.33 | N 8.17 | S 6.25 |
|---|---|---|---|---|
| Found | C 55.76 | H 4.88 | N 8.16 | S 6.34 |

MS (ESI) m/z: 486 (MH⁺).

EXAMPLE 6

2-Methyl-1-(morpholino)prop-2-yl (2S)-2-{4-[(E)-3-(Imidazol-1-yl)prop-1-en-1-yl]-2-(4-fluorophenyl)benzamido}-4-methylsulfanylbutyrate The title compound was prepared from 4-[(E)-3-(imidazol-1-yl)prop-1-en-1-yl]-2-(4-fluorophenyl)benzoic acid and the appropriate amine using a similar method to that of Example 2. Yield: 50%.

¹H NMR (CDCl₃, 400 MHz) δ: 1.42 (6H, m); 1.5–2.3 (4H, m); 2.04 (3H, s); 2.4–2.6 (6H, m); 3.65 (4H, m); 4.54 (1H, m); 4.74 (2H, m); 5.98 (1H, d); 6.3–6.6 (2H, m); 6.9–7.7 (10H, m).

| Anal. Calculated for $C_{32}H_{39}FN_4O_4S$ | C 64.62 | H 6.61 | N 9.42 | S 5.39 |
|---|---|---|---|---|
| Found | C 64.39 | H 6.86 | N 9.55 | S 6.09 |

MS (ESI) m/z: 595 (MH⁺).

EXAMPLE 7

Cyclopentyl (2S)-2-{4-[(E)-3-(Imidazol-1-yl)prop-1-en-1-yl]-2-(4-fluoropheny)benzamido}-4-methylsulfanylbutyrate The title compound was prepared from 4-[(E)-3-(imidazol-1-yl)prop-1-en-1-yl]-2-(4-fluorophenyl)benzoic acid and the appropriate amine using a similar method to that of Example 2. Yield: 50%

¹H NMR (CDCl₃, 400 MHz) δ: 1.5–2.2 (12H, m); 2.03 (3H, s); 4.60 (1H, m); 4.74 (2H, m); 5.12 (1H, m); 6.01 (1H, d); 6.3–6.6 (2H, m); 6.9–7.7 (10H, m).

| Anal. Calculated for $C_{29}H_{32}FN_3O_3S$ | C 66.77 | H 6.18 | N 8.06 | S 6.15 |
|---|---|---|---|---|
| Found | C 67.13 | H 6.57 | N 8.22 | S 6.53 |

MS ESI) m/z: 522 (MH⁺).

EXAMPLE 8 n-Butyl (2S)-2-{4-[(E-3-(Imidazol-1-yl)prop-1-en-1-yl]-2-(4-fluorophenyl)benzamido}-4-methylsulfanylbutyrate The title compound was prepared from 4-[(E)-3-(imidazol-1-yl)prop-1-en-1-yl]-2-(4-fluorophenyl)benzoic acid and the appropriate amine using a similar method to that of Example 2. Yield: 42%

¹H NMR (CDCl₃, 400 MHz) δ: 0.93 (3H, t); 1.30–1.41 (2H, m); 1.54–1.64 (2H, m); 1.75–1.87 (1H, m); 1.92–2.02 (1H, m); 2.03 (3H, s); 2.19 (2H, m); 4.02–4.15 (2H, m); 4.63–4.70 (1H, m); 4.75 (2H, d); 6.01 (1H, d); 6.34–6.44 (1H, m); 6.52 (1H, d); 6.97 (1H, 7.07–7.16 (3H, m); 7.30 (1H, s); 7.35–7.44 (3H, m); 7.55 (1H, s); 7.64 (1H, d).

| Anal. Calculated for $C_{28}H_{32}FN_3O_3S$ | C 65.99 | H 6.33 | N 8.24 | S 6.29 |
|---|---|---|---|---|
| Found | C 65.59 | H 6.43 | N 8.25 | S 6.64 |

MS (ESI) m/z: 510 (MH⁺).

EXAMPLE 9

Prop-2-yl (2S)-2-{4-[(E)-3-(Imidazol-1-yl)prop-1-en-1-yl]-2-(4-fluorophenyl)benzamido}-4-methylsulfanylbutyrate The title compound was prepared from 4-[(E)-3-(imidazol-1-yl)prop-1-en-1-yl]-2-(4-fluorophenyl)benzoic acid and the appropriate amine using a similar method to that of Example 2. Yield: 52%

$^1$H NMR (CDCl$_3$, 400 MHz) δ: 1.24 (6H, m); 1.76–2.06 (2H, m); 2.05 (3H, s); 2.16–2.25 (2H, m); 4.59–4.66 (1H, m); 4.77 (2H, d); 4.99 (1H, m); 6.05 (1H, d);6.36–6.46 (1H, m); 6.53 (1H, d); 6.99 (1H, s); 7.09–7.66 (9H, m).

| Anal. Calculated for C$_{27}$H$_{30}$FN$_3$O$_3$S, 0.16 H$_2$O | C 65.13 | H 6.13 | N 8.44 | S 6.44 |
|---|---|---|---|---|
| Found | C 65.28 | H 6.26 | N 8.50 | S 6.05 |

MS (ESI) m/z: 496 (MH$^+$).

EXAMPLE 10

(2S)-2-{5-[(E)-3-(Imidazol-1-yl)prop-1-en-1-yl]-2-(4-fluorophenethyl)benzamido}-4-methylsulfanylbutyric Acid The title compound was prepared from Example 11 using a similar method to that described in Example 1. Yield:35%.

$^1$H NMR (DMSOd$_6$+CF$_3$COOD, 400 MHz) δ: 1.91–2.15 (2H, m); 2.04 (3H, s); 2.5–2.66 (2H, m); 2.71–2.89 (2H, m); 2.89–3.11 (2H, m); 4.47–4.59 (1H, m); 5.03 (2H, d); 645–6.56 (1H, m); 6.75 (1H, d); 7.0–7.52 (7H, m); 6.74 (1H, s); 7.80 (1H, s); 9.20 (1H, s).

| Anal. Calculated for C$_{26}$H$_{28}$FN$_3$O$_3$S, 2.4 H$_2$O | C 64.85 | H 5.86 | N 8.73 | S 6.66 |
|---|---|---|---|---|
| Found | C 59.50 | H 6.30 | N 8.01 | S 6.11 |

MS (ESI) m/z: 482 (MH$^+$).

EXAMPLE 11 tert-Butyl (2S)-2-{5-[(E)-3-(Imidazol-1-yl)prop-1-en-1-yl]-2-(4-fluorophenethyl)benzamido}-4-methylsulfanylbutyrate A solution of pentafluorophenyl 5-[(E)-3-(imidazol-1-yl)prop-1-en-1-yl]-2-(4-fluorophenethyl)benzoate (0.36 g, 0.7 mmol), L-methionine-tert-butyl ester(0.173 g, 0.84 mmol) and 1-hydroxy-7-azabenzotriazole (0.1 g, 0.73 mmol) in DMF (2 ml) was stirred at ambient temperature overnight. After evaporation of the solvent, the residue was taken up in ethyl acetate, washed with 5% sodium hydrogen carbonate solution and saturated brine and evaporated to dryness. The residue was then purified by flash chromatography eluting with dichloromethane/ethanol (97/3) to give the title compound. Yield: 50%

$^1$H NMR (CDCl$_3$, 400 MHz) δ: 1.49 (9H, s); 1.9–2.3 (2H, m); 2.09 (3H, s); 2.5–2.7 (2H, m); 2.8–3.2 (4H, m); 4.75 (3H, m); 6.2–6.6 (2H, m); 6.9–7.6 (10H, m). MS (ESI) m/z: 538 (MH$^+$).

The starting material was prepared as follows.

Methyl 5-[3-(imidazol-1-yl)prop-1-en-1-yl]-2-(4-fluorophenethyl)benzoate was prepared in a similar way to that described for methyl 4-[3-(imidazol-1-yl)prop-1-en-1-yl]-2-(4-fluorophenyl)benzoate in Example 2 but using 4-(4-fluorophenethyl)-3-methoxycarbonylbenzyl triphenylphosphonium bromide instead of 3-(4-fluorophenyl)4-methoxycarbonylbenzyl triphenylphosphonium bromide. Yield: 70%

$^1$H NMR (CDCl$_3$, 400 MHz) δ: 2.8–2.95 (2H, m); 3.15–3.30 (2H, m); 3.89 and 3.91 (3H, s); 4.7–4.85 (2H, m); 5.8–6.8 (2H, m); 6.9–7.85 (10H, m).

Sodium hydroxide (0.8 g, 20 mmol) in distilled water (3 ml) was added to a solution of methyl 5-[3-(imidazol-1-yl)prop-1-en-1-yl]-2-(4-fluorophenethyl)benzoate (E and Z isomers) (2.4 g;.6.6 mmol) in methanol (30 ml). The mixture was refluxed for 6 hours. After evaporation and acidification with 12N HCl to pH 6, the residue was extracted with dichloromethane and evaporated to dryness to give 5-[3-(imidazol-1-yl)prop-1-en-1-yl]-2-(4-fluorophenethyl) benzoic acid (mixture of E and Z isomers).

$^1$H NMR (DMSOd$_6$+CF$_3$COOD) 400 MHz) δ: 2.75–2.90 (2H, m); 3.1–3.3 (2H, m); 4.95–5.30 (2H, m); 5.90 and 6.5–6.85 (2H, m); 7–7.95 (10H, m); 9.2 (1H, m).

Pentafluorophenyl trifluoroacetate (1.47 ml; 8.6 mmol) was added to a solution of 5-[3-(imidazol-1-yl)prop-1-en-1-yl]-2-(4-fluorophenethyl)benzoic acid (2.5 g, 7.14 mmol) and pyridine (0.7 ml; 8.6 mmol) in DMF (7 ml). After stirring at ambient temperature overnight, the mixture was evaporated to dryness and the residue extracted with ethyl acetate, washed with saturated sodium hydrogen carbonate solution and saturated brine. After evaporation the reaction mixture was purified by flash chromatography, eluting with dichloromethane/ethanol (99/1) to give E isomer pentafluorophenyl 5-[(E)-3-(imidazol-1-yl)prop-1-en-1-yl]-2-(4-fluorophenethyl)benzoate and Z isomer pentafluorophenyl 5-[(Z)-3-(imidazol-1-yl)prop-1-en-1-yl]-2-(4-fluorophenethyl)benzoate. Yield: 68%

E isomer: $^1$H NMR (CDCl$_3$, 400 MHz) δ: 2.88 (2H, m); 3.26 (2H, m); 4.76 (2H, m); 6.3–6.6 (2H, m); 6.9–7.8 (9H, m); 8.17 (1H, d).

Z isomer: $^1$H NMR (CDCl$_3$, 400 MHz) δ: 2.90 (2H, m); 3.27 (2H, m); 4.82 (2H, m); 5.89 (1H, m); 6.78 (1H, m); 6.9–7.6 (9H, m); 8.07 (1H, s).

EXAMPLE 12

(2S)-2-{5-[(E)-3-(Imidazol-1-yl)prop-1-en-1-yl]-2-(4-fluorophenethyl)benzamido}-4-methylsulfonylbutyric Acid The title compound was prepared from Example 13 using a similar method to that described in Example 1. Yield: 60%.

$^1$H NMR (DMSO+CF$_3$COOD, 400 MHz) δ: 2.1–2.35 (2H, m); 2.7–3.1 (4H, m); 3.0 (3H, s); 3.15–3.4 (2H, m); 4.55 (1H, m); 5.04 (2H, m); 6.4–6.8 (2H, m); 7–7.5 (7H, m); 7.7–7.85 (2H, m); 8.8 (1H, m); 9.20 (1H, s).

| Anal. Calculated for C$_{26}$H$_{28}$FN$_3$O$_5$S, 1.9 H$_2$O | C 57.01 | H 5.85 | N 7.67 | S 5.85 |
|---|---|---|---|---|
| Found | C 56.88 | H 5.80 | N 7.79 | S 6.04 |

MS (ESI) m/z: 514 (MH$^+$).

EXAMPLE 13 tert-Butyl (2S)-2-{5-[(E)-3-(Imidazol-1-yl)prop-1-en-1-yl]-2-(4-fluorophenethyl)benzamido}-4-methylsulfonylbutyrate The title compound was prepared from pentafluorophenyl 5-[(E)-3-(imidazol-1-yl)prop-1-en-1-yl]-2-(4-fluorophenethyl)benzoate using a similar method to that described in Example 11. Yield: 44%

$^1$H NMR (CDCl$_3$, 400MHz) δ 1.47 (9H, s); 2.2–2.6 (2H, m); 2.8–3.3 (6H, m); 2.92 (3H, s); 4.73 (3H, m); 6.2–6.6 (2H, m); 6.85–7.6 (10H, m).

| Anal. Calculated for $C_{30}H_{36}FN_3O_5S$, 0.70 $H_2O$ | C 61.88 | H 6.47 | N 7.22 | S 5.51 |
|---|---|---|---|---|
| Found | C 61.66 | H 6.42 | N 7.22 | S 6.18 |

MS (ESI) m/z: 570 (MH$^+$).

EXAMPLE 14

(2S)-2-{5-[(Z)-3-(Imidazol-1-yl)prop-1-en-1-yl]-2-(4-fluorophenethyl)benzamido}-4-methylsulfanylbutyric Acid The title compound was prepared from Example 15 using a similar method to that described in Example 1. Yield: 50%

$^1$HNMR (DMSOd$_6$+CF$_3$COOD, 400 MHz) δ: 1.88–2.16 (2H, m); 2.04 (3H, s); 2.50–2.71 (2H, m); 2.72–3.11 (4H, m); 4.47–4.62 (1H, m); 2H, m); 5.21 (2H, d); 5.83–5.96 (6.80 (1H, d); 7.00–7.39 (7H, m); 7.32 (1H, s); 7.78 (1H, s); 9.19 (1H, s).

| Anal. Calculated for $C_{26}H_{28}FN_3O_3S$, 2.5 $H_2O$ | C 59.30 | H 6.32 | N 7.98 | S 6.00 |
|---|---|---|---|---|
| Found | C 59.28 | H 5.85 | N 7.82 | S 5.87 |

MS (ESI) m/z: 482 (MH$^+$).

EXAMPLE 15 tert-Butyl (2S)-2-{5-[(Z)-3-(Imidazol-1-yl)prop-1-en-1-yl]-2-(4-fluorophenethyl)benzamido}-4-methylsulfanylbutyrate The title compound was prepared from pentafluorophenyl 5-[(Z)-3-(imidazol-1-yl)prop-1-en-1-yl]-2-(4-fluorophenethyl)benzoate and the appropriate amine using a similar method to that described in Example 11. Yield: 67%

$^1$H NMR (CDCl$_3$, 400 MHz) δ: 1.5 (9H, s); 2–2.4 (2H, m); 2.08 (3H, s); 2.4–2.7 (2H, m); 2.8–3.2 (4H, m); 4.75 (3H, m); 5.85 (1H, m); 6.48 (1H, m); 6.6–7.6 (10H, m). MS (ESI) m/z: 538 (MH$^+$).

EXAMPLE 16

(2S)-2-{5-[(Z)-3-Imidazol-1-yl)prop-1-en-1-yl]-2-(4-fluorophenethyl)benzamido}-4-methylsulfonylbutyric Acid The title compound was prepared from Example 17 using a similar method to that described in Example 1.

$^1$H NMR (DMSOd$_6$+CF$_3$COOD, 400 MHz) δ: 2.1–2.4 (2H, m); 2.7–3.45 (6H, m); 3.0 (3H, s); 4.55 (1H, m); 5.22 (2H, m); 5.92 (1H, m); 6.80 (1H, m); 7–7.5 (7H, m); 7.75 (2H, d); 8.8 (1H, d); 9.18 (1H, s).

| Anal. Calculated for $C_{26}H_{28}FN_3O_5S$, $H_2O$ | C 58.74 | H 5.69 | N 7.90 | S 6.03 |
|---|---|---|---|---|
| Found | C 58.74 | H 5.65 | N 8.03 | S 6.08 |

MS (ESI) m/z: 514 (MH$^+$).

EXAMPLE 17 tert-Butyl (2S)-2-{5-[(Z)-3-(Imidazol-1-yl)prop-1-en-1-yl]-2-(4-fluorophenethyl)benzamido}-4-methylsulfonylbutyrate The title compound was prepared from pentafluorophenyl 5-[(Z)-3-(imidazol-1-yl)prop-1-en-1-yl]-2-(4-fluorophenethyl)benzoate and the appropriate amine using a similar method to that described in Example 11. Yield: 65%

$^1$H NMR (CDCl$_3$, 400 MHz) δ: 1.52 (9H, s); 2.2–2.6 (2H, m); 2.8–3.30 (6H, m); 3.05 (3H, s); 4.7–4.9 (3H, m); 5.85 (1H, m); 6.6–7.35 (11H, m); 7.49 (1H, s).

| Anal. Calculated for $C_{30}H_{36}FN_3O_5S$, 0.2 $H_2O$ | C 62.85 | H 6.40 | N 7.33 | S 5.60 |
|---|---|---|---|---|
| Found | C 62.87 | H 6.58 | N 7.33 | S 6.06 |

MS (ESI) m/z: 570 (MH$^+$).

EXAMPLE 18

(2S)-2-{4-[(E)-3-(1-Methylimidazol-2-yl)prop-1-en-1-yl]-2-(4-fluorophenyl)benzamido}-4-methylsulfanylbutyric Acid The title compound was prepared from Example 19 using a similar method to that described in Example 1.

$^1$H NMR (DMSOd$_6$+CF$_3$COOD, 400 MHz) δ: 1.74–2.0 (2H, m); 2.01 (3H, s); 2.16–2.37 (2H, m); 3.83 (3H, s); 3.98 (2H, d); 4.32 (1H, dd); 6.48–6.60 (1H, m); 6.69 (1H, d); 7.13–7.26 (2H, m); 7.40 –7.57 (5H, m); 7.63 (1H, d); 7.67 (1H, d).

| Anal. Calculated for $C_{25}H_{26}FN_3O_3S$, 1.15 $H_2O$ | C 61.50 | H 5.84 | N 8.61 | S 6.57 |
|---|---|---|---|---|
| Found | C 61.53 | H 6.08 | N 8.54 | S 6.57 |

MS (ESI) m/z: 468 (MH$^+$).

EXAMPLE 19 tert-Butyl (2S)-2-{4-[(E)-3-(1-Methylimidazol-2-yl)prop-1-en-1-yl]-2-(4-fluorophenyl)benzamido}-4-methylsulfanylbutyrate The title compound was prepared from 4-[3-(1-methylimidazol-2-yl)prop-1-en-1-yl]-2-fluorophenyl)benzoic acid using a similar method to that described in Example 2. Yield: 30%

$^1$H NMR (CDCl$_3$+CF$_3$COOD, 400 MHz) δ: 1.46 (9H, s); 1.75–1.99 (2H, m); 2.05 (3H, s); 2.07–2.33 (2H, m); 3.86 (3H, s); 3.97 (2H, d); 4.59 (1H, dd); 6.24–6.33 (1H, m); 6.63 (1H, d); 7.09–7.17 (3H, m); 7.29–7.44 (5H, m).

| Anal. Calculated for $C_{29}H_{34}FN_3O_3S$, 0.3 $H_2O$ | C 64.95 | H 6.65 | N 7.84 | S 5.98 |
|---|---|---|---|---|
| Found | C 64.85 | H 6.52 | N 7.81 | S 5.94 |

MS (ESI) m/z: 524 (MH$^+$).

The starting material was prepared as follows:

A mixture of 4-(4-fluorophenethyl)-3-methoxycarbonylbenzyl triphenylphosphonium bromide (27 g, 46 mmol), glycolaldehyde (7.2 g; 92 mmol), potassium carbonate (13 g; 92 mmol) and 18-crown-6 (0.2 g) in dichloromethane (300 ml) was stirred for 2 days at ambient temperature under argon atmosphere. After addition of distilled water and extraction, the solution was evaporated to dryness to give methyl 2-(4-fluorophenyl)-4-(3-hydroxyprop-1-en-1-yl)benzoate which was used in the next step without further purification.

A solution of methyl 2-(4-fluorophenyl)-4-(3-hydroxyprop-1-en-1-yl)benzoate (17 g), triphenylphosphine (22.8 g; 87 mmol) and tetrabromomethane (28.8 g; 87 mmol) in dichloromethane (200 ml) was stirred at 0° C. for 1 hour. After filtration of the insoluble material and evaporation to dryness, the residue was purified by flash chromatography eluting with dichloromethanelpetroleum ether (30/70) to give methyl 2-(4-fluorophenyl)-4-(3-bromoprop-1-en-1-yl)benzoate as a mixture of E and Z isomers.

$^1$H NMR (CDCl$_3$, 400 MHz) δ: 3.65 (3H, m); 4.15 (2H, m); 6.1–6.2 and 6.4–6.7 (2H, m); 7–7.95 (7H, m). n-Butyl lithium (1.6 M solution in ether, 30 ml) was added at −78° C. and under argon atmosphere to a solution of N-methylimidazole (3.2 ml; 40 mmol). After stirring at −78° C. for 45 minutes, zinc iodide (14 g; 44 mmol) in solution in THF (100 ml) was added. The mixture was allowed to warm to ambient temperature for 1 hour, cooled down to −78° C., and a solution of copper (I) cyanide (0.72 g; 8 mmol) and lithium chloride (0.68 g; 1.6 mmol) in THF (10 ml) was then added at −78° C. followed by a solution of methyl 2-(4-fluorophenyl)-4-(3-bromoprop-1-en-1-yl)benzoate (7 g; 20 mmol) in THF (50 ml). The mixture was stirred at −78° C., for 30 minutes and for 1 hour 30 minutes at room temperature. After evaporation of the solvent, the residue was treated with EDTA (17 g; 44 mmol) in distilled water (50 ml) and extracted with dichloromethane. The organic layer was evaporated and purified by flash chromatography eluting with dichloromethane/ethanol (98/2) to give methyl 4-[3-(1-methylimidazol-2-yl)prop-1-en-1-yl]-2-(4-fluorophenyl)benzoate as a mixture of E and Z isomers. Yield: 71%

$^1$H NMR (CDCl$_3$, 400 MHz) δ: 3.5–3.8 (8H, m); 6.05 and 6.7 (1H, m); 6.8–7.9 (9H, m).

Methyl 4-[3-(1-methylimidazol-2-yl)prop-1-en-1-yl]-2-(4-fluorophenyl)benzoate (5 g; 14.3 mmol) in solution in methanol (100 ml) was treated at reflux for 4 hours with sodium hydroxide (1.2 g; 30 mmol) in solution in distilled water (10 ml). After evaporation to dryness, the residue was acidified at pH 6 with 6 N HCl to give a solid which was triturated in water and subsequently in ether to give 4-[3-(1-methylimidazol-2-yl)prop-1-en-1-yl]-2-(4-fluorophenyl)benzoic acid as a solid (mixture of E and Z isomers).

$^1$H NMR (DMSOd$_3$+CF$_3$COOD, 400 MHz) δ: 3.82 and 3.84 (3H, s); 4.0 (2H, m); 6.5–7.9 (11H, m). MS (ESI) m/z: 336 (MH$^+$).

EXAMPLE 20

(2S)-2-{4-[(E)-3-(Imidazol-2-yl)prop-1-en-1-yl]-2-(4-fluorophenyl)benzamido}-4-methylsulfanylbutyric Acid The title compound was prepared from Example 21 using a similar method to that described in Example 1. Yield: 34%

$^1$H NMR (DMSOd$_6$+CF$_3$COOD, 400 MHz) δ: 1.73–2.08 (2H, m); 2.0 (3H, s); 2.14–2.37 (2H, m); 3.93 (2H, d); 4.31 (1H, dd); 6.52–6.63 (1H, m); 6.71 (1H, d); 7.14–7.24 (2H, m); 7.40–7.55 (5H, m); 7.63 (2H, s).

| Anal. Calculated for C$_{24}$H$_{24}$FN$_3$O$_3$S, 1.2 H$_2$O | C 59.99 | H 5.66 | N 8.74 | S 6.67 |
|---|---|---|---|---|
| Found | C 59.99 | H 5.65 | N 8.62 | S 6.42 |

MS (ESI) m/z: 454 (MH$^+$).

EXAMPLE 21 tert-Butyl (2S)-2-{4-[(E)-3-(Imidazol-2-yl)prop-1-en-1-1-yl]-2-(4-fluorophenyl)benzamido}-4-methylsulfanylbutyrate The title compound was prepared from 4-[(E)-3-(imidazol-2-yl)prop-1-en-1-yl]-2-(4-fluorophenyl)benzoic acid and the appropriate amine using a similar method to that described in Example 2. Yield: 75%

$^1$H NMR (CDCl$_3$, 400 MHz) δ: 1.42 (9H, s); 1.76–2.03 (2H, m); 2.05 (3H, s); 2.17–2.26 (2H, m); 3.70 (2H, d); 4.50–4.59 (1H, m); 6.04 (1H, d); 6.39–6.49 (1H, m); 6.53 (1H, d); 7.0 (2H, s); 7.04–7.43 (6H, m); 7.59 (1H, d).

| Anal. Calculated for C$_{28}$H$_{32}$FN$_3$O$_3$S | C 65.99 | H 6.33 | N 8.24 | S 6.29 |
|---|---|---|---|---|
| Found | C 65.64 | H 6.50 | N 8.16 | S 5.33 |

MS (ESI) m/z: 510 (MH$^+$).

The starting material was prepared as follows:

Methyl 4-[(E)-3-(1-tritylimidazol-2-yl)prop-1-en-1-yl]-2-(4-fluorophenyl)benzoate was prepared from methyl 2-(4-fluorophenyl)-4-(3-bromoprop-1-en-1-yl)benzoate using a similar method to that described for methyl 4-[3-(1-methylimidazol-2-yl)prop-1-en-1-yl]-2-(4-fluorophenyl)benzoate in Example 21, but using N-tritylimidazole in replacement of N-methylimidazole.

$^1$H NMR (CDCl$_3$+CF$_3$COOD, 400 MHz) δ: 3.66 (2H, m); 3.68 (3H, s); 6.14 (1H, d); 7–7.9 (25H, m). MS (ESI) m/z: 579 (MH$^+$).

A solution of methyl 4-[(E)-3-(1-tritylimidazol-2-yl)prop-1-en-1-yl]-2-(4-fluorophenyl)benzoate (5.78 g; 6.5 mmol), acetic acid (5 ml) and 12N HCl (5 ml) in methanol (100 ml) was refluxed for 1 hour 30 minutes. After evaporation to dryness, the residue was neutralised with aqueous NH$_4$OH, extracted with dichloromethane, evaporated and purified by flash chromatography, eluting with dichloromethane/ethanol (98/2) to give methyl 4-[(E)-3-(imidazol-2-yl)prop-1-en-1-yl]-2-(4-fluorophenyl)benzoate. Yield: 63%

$^1$H NMR (CDCl$_3$, 400 MHz) δ: 3.72 (3H, s); 3.91 (2H, m); 6.28 (1H, m); 6.67 (1H, d); 7–7.45 (8H, m); 7.75 (1H, d).

A solution of methyl 4-[(E)-3-(imidazol-2-yl)prop-1-en-1-yl]-2-(4-fluorophenyl)benzoate (1.37 g; 4 mmol) in methanol (20 ml) was treated at reflux for 4 hours with a solution of sodium hydroxide (0.32 g; 8 mmol) in water (24 ml). After evaporation to dryness the residue was acidified at pH 6 with 12N HCl. The resulting solid was triturated with water and subsequently with ether to give 4-[(E)-3-(imidazol-2-yl)prop-1-en-1-yl]-2-(4-fluorophenyl)benzoic acid. Yield: 46%

$^1$H NMR (DMSOd$_3$+CF$_3$COOD, 400 MHz) δ: 3.94 (2H, m); 6.4–6.8 (1H, m); 7–7.9 (10H, m).

EXAMPLE 22

(2S)-2-{4-[(E)-3-(Imidazol-1-yl)prop-1-en-1-yl]-2-(2,4-difluorolphenyl)benzamido}-4-methylsulfanylbutyric Acid The title compound was prepared from Example 23 using a similar method to that described in Example 1. Yield: 64%.

$^1$H NMR (DMSOd$_6$+CF$_3$COOD, 400 MHz) δ: 1.73–2.03 (2H, m); 2.02 (3H, s); 2.23–2.43 (2H, m); 4.32 (1H, dd); 5.06 (2H, d); 6.62–6.73 (1H, m); 6.78 (1H, d); 7.03–7.14 (1H, m); 7.16–7.28 (1H, m); 7.35–7.44 (1H, m); 7.49 (1H, s); 7.55–7.65 (2H, m); 7.74 (1H, s); 7.81 (1H, s); 9.21 (1H, s).

| Anal. Calculated for C$_{24}$H$_{23}$F$_2$N$_3$O$_3$S, 0.5 H$_2$O | C 59.99 | H 5.03 | N 8.74 | S 6.67 |
|---|---|---|---|---|
| Found | C 60.19 | H 5.11 | N 8.65 | S 6.28 |

MS (ESI) m/z: 472 (MH$^+$).

EXAMPLE 23 tert-Butyl (2S)-2-{4-[(E)-3-(Imidazol-1-yl)prop-1-en-1-yl]-2-(2,4-difluorophenyl)benzamido}-4-methylsulfanylbutyrate The title compound was prepared from 4-[(E)-3-(imidazol-1-yl)prop-1-en-1-yl]-2-(2,4-difluorophenyl)benzoic acid and the appropriate amine using a similar method to that described in Example 2. Yield: 74%

$^1$H NMR (CDCl$_3$, 400 MHz) δ: 1.44 (9H, s); 1.79–2.12 (2H, m); 2.07 (3H, s); 2.25–2.42 (2H, m); 4.53–4.62 (1H, m); 4.75 (2H, d); 6.27 (1H, d); 6.33–6.44 (1H, m); 6.51 (1H, d); 6.82–7.04 (3H, m); 7.11 (1H, s); 7.27–7.38 (2H, m); 7.40–7.48 (11H, dd); 7.55 (1H, s); 7.67 (1H, d).

| Anal. Calculated for C$_{28}$H$_{31}$F$_2$N$_3$O$_3$S | C 63.74 | H 5.92 | N 7.96 | S 6.08 |
|---|---|---|---|---|
| Found | C 63.38 | H 5.90 | N 7.85 | S 5.72 |

MS (ESI) m/z: 528 (MH$^+$).

The starting material was prepared as follows:

A mixture of 2-(imidazol-1-yl)acetaldehyde (2.32 g; 76 mmol), 4-methoxycarbonyl-3-(4-trifluoromethylsulphonyloxy)benzyl triphenylphosphonium bromide (5.27 g; 37 mmol), potassium tert-butoxide (1.2 g; 10 mmol) in dichloromethane (30 ml) was stirred under argon atmosphere at ambient temperature for 7 hours. After filtration of the insoluble, and evaporation, the residue was purified by flash chromatography eluting with isopropanol/dichloromethane (4/96) to give methyl 4-[3-(imidazol-1-yl)prop-1-en-1-yl]-2-(trifluoromethylsulphonyloxy)benzoate as a mixture of E and Z isomers.

$^1$H NMR (CDCl$_3$, 400 MHz) δ: 3.98 (3H, s); 4.80 (2H, m); 6–8.2 (8H, m).

A mixture of methyl 4-[3-(imidazol-1-yl)prop-1-en-1-yl]-2-(trifluoromethylsulphonyloxy)benzoate (1.17 g; 3 mmol), 2,4-difluorophenylboronic acid (0.52 g; 3.3 mmol), tetrakis(triphenylphosphine) palladium (0.14 g; 0.12 mmol), 2M aqueous sodium carbonate solution (4.5 ml), lithium chloride (0.25 g; 6 mmol) and ethanol (13 ml) in toluene (120 ml) was refluxed, under an argon atmosphere, for 8 hours. The mixture was extracted with ethyl acetate and purified by flash chromatography eluting with isopropanol/dichloromethane (3/97) to give methyl 4-[(E)-3-(imidazol-1-yl)prop-1-en-1-yl]-2-(2,4-difluorophenyl)benzoate as a mixture of E and Z isomers.

$^1$HNMR (CDCl$_3$, 400 MHz) δ: 3.71 (3H, s); 4.7–4.9 (2H, M); 5.9–6 (1H, m); 6.48.1 (10H, m).

A solution of methyl 4-[(E)-3-(imidazol-1-yl)prop-1-en-1-yl]-2-(2,4-difluorophenyl)benzoate (0.9 g; 2.54 mmol) and 2N sodium hydroxide solution (3.8 ml) in methanol was heated at reflux for 7 hours. After evaporation of the solvent and neutralisation to pH 6.5 with 6N HCl, the residue was purified on reverse phase silica eluting with methanol/ammonium carbonate buffer (2 g/l, pH 7) (50/50) to give 4-[(E)-3-(imidazol-1-yl)prop-1-en-1-yl]-2-(2,4-difluorophenyl)benzoic acid after freeze-drying. Yield: 49%.

$^1$H NMR (DMSO+CF$_3$COOD, 400 MHz) δ: 5.06 (2H, m); 6.75 (2H, m); 7–8 (8H, m); 9.20 (1H, s).

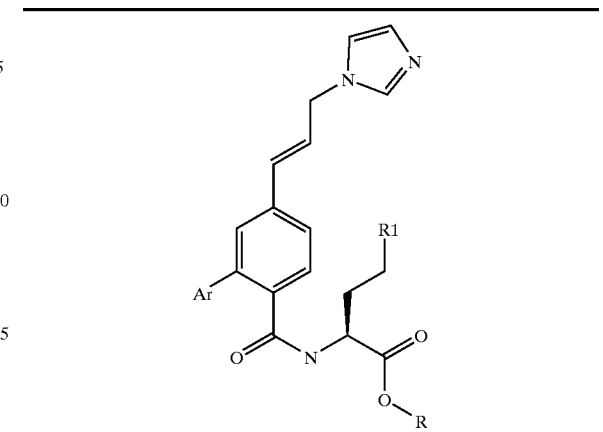

| Example | Ar | R | R1 |
|---|---|---|---|
| 22 | 2,4-difluorophenyl | H | SCH$_3$ |
| 23 | 2,4-difluorophenyl | t-Bu | SCH$_3$ |
| 24 | 2-thienyl | t-Bu | SCH$_3$ |
| 25 | 4-chlorophenyl | H | SCH$_3$ |
| 26 | 4-chlorophenyl | t-Bu | SCH$_3$ |
| 27 | 3-chloro-4-fluorophenyl | H | SCH$_3$ |
| 28 | 3-chloro-4-fluorophenyl | t-Bu | SCH$_3$ |
| 29 | 2,4-dichlorophenyl | H | SCH$_3$ |
| 30 | 2,4-dichlorophenyl | t-Bu | SCH$_3$ |
| 31 | 2,4-dichlorophenyl | t-Bu | SO$_2$CH$_3$ |
| 32 | 3-thienyl | H | SCH$_3$ |
| 33 | 3-thienyl | t-Bu | SCH$_3$ |
| 34 | 3-chlorophenyl | H | SCH$_3$ |
| 35 | 3-chlorophenyl | t-Bu | SCH$_3$ |

EXAMPLE 24 tert-Butyl (2S)-2-{4-[(E)-3-(Imidazol-1-yl)prop-1-en-1-yl]-2-(thien-2-yl)benzamido}-4-methylsulfanylbutyrate The title compound was prepared using a similar method to that described in Example 23, except using the appropriate boronic acid in place of 2,4-difluorophenylboronic acid.

Yield: 53%; $^1$H NMR (CDCl$_3$, 400 MHz) δ: 1.43 (9H, s); 1.78–2.08 (2H, m); 2.05 (3H, s); 2.19–2.32 (2H, m); 4.58–4.66 (1H, m); 4.75 (2H, d); 6.18 (1H, d); 6.33–6.44 (1H, m); 6.51 (1H, d); 6.97 (1H, s); 6.04–6.18 (3H, m); 6.35–6.45 (3H, m); 7.55 (1H, s); 7.61 (1H, d).

| Anal. Calculated for C$_{26}$H$_{31}$N$_3$O$_3$S$_2$ | C 62.75 | H 6.28 | N 8.44 | S 12.89 |
|---|---|---|---|---|
| Found | C 62.01 | H 6.91 | N 8.62 | S 12.65 |

MS (ESI) m/z: 498 (MH$^+$).

EXAMPLE 25

(2S)-2-{4-[(E)-3-(Imidazol-1-yl)prop-1-en-1-yl]-2-(4-chlorophenyl)benzamido}-4-methylsulfanylbutyric Acid The title compound was prepared from Example 26 as described for Example 1.

Yield: 54%; $^1$H NMR (DMSOd$_6$+CF$_3$COOD, 400 MHz) δ: 1.75–2.05 (2H, m); 2.02 (3H, s); 2.15–2.40 (2H, s);

4.26–4.37 (1H, s); 5.06 (2H, s); 6.62–6.74 (1H, m); 6.79 (1H, d); 7.38–7.62 (7H, m); 7.75 (1H, s); 7.81 (1H, s); 9.22 (1H, s).

| Anal. Calculated for $C_{24}H_{24}ClN_3O_3S$, 0.8 $H_2O$ | C 59.51 | H 5.15 | N 8.67 | S 6.62 |
|---|---|---|---|---|
| Found | C 59.14 | H 5.17 | N 9.41 | S 5.96 |

MS (ESI) m/z: 469 (MH$^+$).

EXAMPLE 26 tert-Butyl (2S)-2-{4-[(E)-3-(Imidazol-1-yl)prop-1-en-1-yl]-2-(4-chlorophenyl)benzamido}-4-methylsulfanylbutyrate The title compound was prepared using a similar method to that described in Example 23, except using the appropriate boronic acid in place of 2,4-difluorophenylboronic acid.

Yield: 78%; $^1$H N (CDCl$_3$, 400 MHz) δ: 1.43 (9H, s); 1.76 (2H, m); 2.06 (3H, s); 2.22 (2H, m); 4.52–4.59 (1H, m); 4.76 (2H, d); 6.03 (1H, d); 6.34–6.45 (1H, m); 6.97 (1H, s); 7.12 (1H, s); 7.25–7.46 (6H, m); 7.55 (1H, s); 7.64 (1H, d).

| Anal. Calculated for $C_{28}H_{32}ClN_3O_3S$ | C 63.93 | H 6.13 | N 7.99 | S 6.09 |
|---|---|---|---|---|
| Found | C 63.93 | H 6.27 | N 8.16 | S 5.89 |

MS (ESI) m/z: 527 (MH$^+$).

EXAMPLE 27

(2S)-2-{4-[(E)-3-Imidazol-1-yl)prop-1-en-1-yl]-2-(3-chloro-4-fluorophenyl)benzamido}-4-methylsulfanylbutyric Acid The title compound was prepared from Example 28 as described for Example 1.

Yield: 71%; $^1$H NMR (DMSOd$_3$+CF$_3$COOD, 400 MHz) δ: 1.74–2.05 (2H, m); 2.00 (3H, s); 2.15–2.37 (2H, m);4.28–4.37 (1H, m); 5.06 (2H, d); 6.64–6.74 (1H, m); 6.78 (1H, d); 7.35–7.63 (6H, m); 7.75 (1H, s); 7.81 (1H, s); 9.21 (1H, s).

| Anal. Calculated for $C_{24}H_{23}ClFN_3O_3S$, 2 $H_2O$ | C 55.01 | H 5.19 | N 8.02 | S 6.12 |
|---|---|---|---|---|
| Found | C 52.64 | H 4.46 | N 7.80 | S 5.76 |

MS (ESI) m/z: 480 (MH$^+$).

EXAMPLE 28 tert-Butyl (2S)-2-{4-[(E)-3-(Imidazol-1-yl)prop-1-en-1-yl]-2-(3-chloro-4-fluorophenyl)benzamido}-4-methylsulfanylbutyrate The title compound was prepared using a similar method to that described in Example 23, except using the appropriate boronic acid in place of 2,4-difluorophenylboronic acid.

Yield: 83%; $^1$H NMR (CDCl$_3$, 400 MHz) δ: 1.43 (9H, s); 1.77–2.15 (4H, m); 2.06 (3H, s); 2.21–2.37 (2H, m); 4.51–4.63 (1H, m); 4.75 (2H, d); 6.13 (1H, d); 6.34–6.44 (1H, m); 6.50 (1H, d); 6.97 (1H, s); 7.12 (1H, s); 7.14–7.33 (3H, m); 7.38–7.49 (2H, m); 7.55 (1H, s); 7.61 (1H, d).

| Anal. Calculated for $C_{28}H_{31}ClFN_3O_3S$ | C 61.81 | H 5.74 | N 7.72 | S 5.89 |
|---|---|---|---|---|
| Found | C 61.45 | H 5.91 | N 7.67 | S 5.81 |

MS (ESI) m/z: 544 (MH$^+$).

EXAMPLE 29

(2S)-2-{4-[(E)-3-(Imidazol-1-yl)prop-1-en-1-yl]-2-(2,4-dichlorophenyl)benzamido}-4-methylsulfanylbutyric Acid The title compound was prepared from Example 30 as described for Example 1.

Yield: 63%; $^1$H NMR (DMSOd$_3$+CF$_3$COOD, 400 MHz) δ: 1.77–2.08 (2H, m); 2.02 (3H, s); 2.27–2.55 (2H, m); 4.27–4.36 (1H, m); 5.05 (2H, d); 6.59–6.69 (1H, m); 6.78 (1H, d); 7.29–7.82 (8H, m);9.17(1H, s).

| Anal. Calculated for $C_{24}H_{23}Cl_2N_3O_3S$ 0.7 $H_2O$ | C 57.15 | H 4.60 | N 8.33 | S 6.33 |
|---|---|---|---|---|
| Found | C 55.42 | H 4.78 | N 8.40 | S 6.20 |

MS (ESI) m/z: 505 (MH$^+$).

EXAMPLE 30 tert-Butyl (2S)-2-{4-[(E)-3-(Imidazol-1-yl)prop-1-en-1-yl]-2-(2,4-dichlorophenyl)benzamido}-4-methylsulfanylbutyrate The title compound was prepared using a similar method to that described in Example 23, except using the appropriate boronic acid in place of 2,4-difluorophenylboronic acid.

Yield: 85%; $^1$H N (CDCl$_3$, 400 MHz) δ: 1.43 (9H, s); 1.70–2.43 (4H, m); 2.44 (3H, s); 4.45–4.59 (1H, s); 4.73 (2H, d); 6.08–6.28 (1H, m); 6.31–6.42 (1H, m); 6.51 (1H, d); 6.95 (1H, s); 7.10 (1H, s); 7.19–7.50 (3H, m); 7.41–7.50 (2H, m); 7.52 (1H, s); 7.62–7.77 (1H, m).

| Anal. Calculated for $C_{28}H_{31}Cl_2N_3O_3S$ | C 60.00 | H 5.57 | N 7.50 | S 5.72 |
|---|---|---|---|---|
| Found | C 59.97 | H 5.74 | N 7.58 | S 5.64 |

MS (ESI) m/z: 560 (MH$^+$).

EXAMPLE 31 tert-Butyl (2S)-2-{4-[(E)-3-(Imidazol-1-yl)prop-1-en-1-1-yl]-2-(2,4-dichlorophenyl)benzamido}-4-methylsulfonylbutyrate The title compound was prepared from Example 30 as described for Example 4.

Yield: 71%; $^1$H NMR (CDCl$_3$, 400 MHz) δ: 1.45 (9H, s); 1.90–2.10 (1H, m); 2.24–2.45 (1H, m); 2.65–3.12 (7H, m); 4.41–4.59 (1H, m); 4.73 (2H, d); 6.18–6.54 (3H, m); 6.95 (1H, s); 7.10 (1H, s); 7.15–7.80 (7H, m).

| Anal. Calculated for $C_{28}H_{31}Cl_2N_3O_3S$ | C 56.76 | H 5.27 | N 7.09 | S 5.41 |
|---|---|---|---|---|
| Found | C 56.83 | H 5.52 | N 7.00 | S 5.79 |

MS (ESI) m/z: 592 (MH+).

EXAMPLE 32

(2S)-2-{4-[(E)-3-(Imidazol-1-yl)prop-1-en-1-yl]-2-(thien-3-yl)benzamido}-4-methylsulfanylbutyric Acid The title compound was prepared from Example 33 as described for Example 1.

Yield: 53%; $^1$H NMR (CDCl$_3$, 400 MHz) δ: 1.43 (9H, s); 1.75–2.04 (2H, m); 2.06 (3H, s); 2.18–2.28 (2H, m); 4.55–4.62 (1H, m); 4.75 (2H, d); 6.08 (1H, d); 6.33–6.43 (1H, m); 6.51 (1H, d); 6.97 (1H, s); 7.11 (1H, s); 7.14–7.19 (1H, m); 7.33–7.41 (4H, m); 7.55 (1H, s); 7.63 (1H, d).

| Anal. Calculated for $C_{22}H_{23}N_3O_3S_2$ | C 59.84 | H 5.25 | N 9.52 | S 14.52 |
|---|---|---|---|---|
| Found | C 57.81 | H 5.49 | N 9.15 | S 14.06 |

MS (ESI) m/z: 442 (MH+).

EXAMPLE 33 tert-Butyl (2S)-2-{4-[(E)-3-(Imidazol-1-yl)prop-1-en-1-yl]-2-(thien-3-yl)benzamido}-4-methylsulfanylbutyrate The title compound was prepared using a similar method to that described in Example 23, except using the appropriate boronic acid in place of 2,4-difluorophenylboronic acid.

Yield: 72%; $^1$H NMR (DMSOd$_3$+CF$_3$COOD, 400 MHz) δ: 1.80–2.10 (2H, m); 2.03 (3H, s); 2.28–2.51 (2H, m); 4.33–4.45 (1H, m); 5.06 (2H, d); 6.62–6.72 (1H, m); 6.78 (1H, d); 7.30 (1H, d); 7.99 (1H, d); 7.46–7.57 (2H, m); 7.60–7.66 (2H, m); 7.75 (1H, s); 7.28 (1H, s); 8.65 (1H, d); 9.22 (1H, s).

| Anal. Calculated for $C_{26}H_{31}N_3O_3S_2$ | C 62.75 | H 6.28 | N 8.44 | S 12.89 |
|---|---|---|---|---|
| Found | C 62.31 | H 6.45 | N 8.38 | S 12.72 |

MS (ESI) m/z: 498 (MH+).

EXAMPLE 34

(2S)-2-{4-[(E)-3-(Imidazol-1-yl)prop-1-en-1-yl]-2-(3-chlorophenyl)benzamido}-4-methylsulfanylbutyric Acid The title compound was prepared from Example 35 as described for Example 1.

Yield: 56%; $^1$H NMR (DMSOd$_6$+CF$_3$COOD, 400 MHz) δ: 1.75–2.04 (2H, m); 2.10 (3H, s); 2.15–2.40 (2H, m); 4.25–4.40 (1H, dd); 5.06 (2H, d); 6.6–6.9 (2H, m); 7.28–7.70 (7H, m); 7.75 (1H, s); 7.81 (1H, s); 9.22 (1H, s). MS (ESI) m/z: 470 (MH+).

EXAMPLE 35 tert-Butyl (2S)-2-{4-[(E)-3-(Imidazol-1-yl)prop-1-en-1-yl-2-(3-chlorophenyl)benzamido}-4-methylsulfanylbutyrate The title compound was prepared using a similar method to that described in Example 23, except using the appropriate boronic acid in place of 2,4-difluorophenylboronic acid.

Yield: 74%; $^1$H NMR (CDCl$_3$, 400 MHz) δ: 1.4 (9H, s); 1.74–1.88 (1H, m); 1.89–2.05 (1H, m); 2.04 (3H, s); 2.13–2.28 (2H, m); 4.5–4.6 (1H, m); 4.78 (2H, d); 6.04 (1H, d); 6.3–6.6 (2H, m); 6.90 (1H, s); 7.12 (1H, s); 7.2–7.5 (6H, m); 7.55 (1H, s); 7.64 (1H, d).

| Anal. Calculated for $C_{28}H_{32}ClN_3O_3S$ | C 63.93 | H 6.13 | N 7.99 | |
|---|---|---|---|---|
| Found | C 63.75 | H 6.16 | N 8.08 | |

MS (ESI) m/z: 526 (MH+).

EXAMPLE 36

(2S)-2-{4-[(E)-3-(Imidazol-5-yl)prop-1-en-1-yl]-2-(4-fluorophenyl)benzamido}-4-methylsulfanylbutyric Acid The title compound was prepared from Example 37 as described for Example 1.

Yield: 42%; $^1$H NMR (DMSOd$_3$+CF$_3$COOD, 400 MHz) δ: 1.72–2.13 (2H, m); 2.01 (3H, s); 2.1–2.4 (2H, m); 3.66 (2H, d); 4.23–4.44 (1H, m); 6.45–6.72 (2H, m); 7.08–7.30 (2H, m); 7.31–7.69 (6H, m); 9.06 (1H, s).

| Anal. Calculated for $C_{24}H_{24}CN_3O_3S$ 0.9 $H_2O$ | C 61.37 | H 5.54 | N 8.95 | S 6.83 |
|---|---|---|---|---|
| Found | C 61.07 | H 5.17 | N 8.87 | S 6.62 |

MS (ESI) m/z: 454 (MH+).

EXAMPLE 37 tert-Butyl (2S)-2-{4-[(E)-3-(Imidazol-5-yl)prop-1-en-1-yl]-2-(4-fluorophenyl)benzamido}-4-methylsulfanylbutyrate The title compound was prepared from 4-[(E)-3-(imidazol-5-yl)prop-1-en-1-yl]-2-(4-fluorophenyl)benzoic acid and the appropriate amine as described for Example 2.

Yield: 46%; $^1$H NMR (CDCl$_3$+CF$_3$COOD, 400 MHz) δ: 1.48 (9H, s); 1.7–2.0 (2H, m); 2.06 (3H, s); 2.05–2.26 (2H, m); 3.62–3.81 (3H, m); 4.54–4.67 (1H, m); 6.26–6.45 (1H, m); 7.03–7.66 (8H, m); 8.78 (1H, s). 6.65 (1H, d);

| Anal. Calculated for $C_{28}H_{32}FN_3O_3S$ | C 65.99 | H 6.33 | N 8.24 | S 6.29 |
|---|---|---|---|---|
| Found | C 65.61 | H 6.18 | N 8.24 | S 5.73 |

MS (ESI) m/z: 510 (MH+).

The starting material was prepared as follows:

Ethyl magnesium bromide (3M solution in ether; 5.7 ml; 17 mmol) was added dropwise at 0° C. under argon atmosphere to a solution of N-trityl 5-iodoimidazole (6.1 g; 14 mmol). After stirring at 0° C. for 1 hour, a solution of copper (I) cyanide (0.27 g; 3 mmol) and lithium chloride (0.252 g; 6 mmol) in THF (5 ml) was added. The mixture was cooled down to −78° C. and a solution of methyl 4-(3-bromoprop-1-en-1-yl)-2-(4-fluorophenyl)benzoate (3.5 g; 10 mmol) in THF (10 ml) was added. After stirring at −78° C. for 15 minutes, the temperature was allowed to raise to room temperature. The mixture was stirred further overnight. After addition of aqueous ammonium chloride solution and evaporation to dryness, the residue was extracted with dichloromethane/distilled water. The organic layer was evaporated to give methyl 4-[(E)-3-(1-tritylimidazol-5-yl)prop-1-en-1-yl]-2-(4-fluorophenyl)benzoate which was used in the next step without further purification.

$^1$H NMR (CDCl$_3$+CF$_3$COOD, 400 MHz) δ: 1.48 (9H, s); 3.60–3.82 (5H, m); 7.00–7.85 (26H, m).

A solution of methyl 4-[(E)-3-(1-tritylimidazol-5-yl)prop-1-en-1-yl]-2-(4-fluorophenyl)benzoate (7.8 g; 10 mmol), 12N HCl (7.5 ml) and acetic acid (7.5 ml) in methanol (150 ml) was refluxed for 1 hour 30 minutes. After evaporation to dryness and neutralisation with an aqueous solution of ammonium hydroxide, the residue was extracted with dichloromethane and purified by flash chromatography, eluting with a gradient 2–5% ethanol/dichloromethane to give methyl 4-[(E)-3-(imidazol-5-yl)prop-1-en-1-yl]-2-(4-fluorophenyl)benzoate. Yield: 20%.

$^1$H NMR (CDCl$_3$, 400 MHz) δ: 3.5–3.8 (5H, m); 6.58 (2H, m); 6.8–7.9 (9H, m).

A solution of methyl 4-[(E)-3-(imidazol-5-yl)prop-1-en-1-yl]-2-(4-fluorophenyl)benzoate (0.6 g; 1.8 mmol) in 1N HCl (15 ml) was refluxed for 20 hours. The mixture was evaporated to dryness to give 4-[(E)-3-(imidazol-5-yl)prop-1-en-1-yl]-2-(4-fluorophenyl)benzoic acid as the hydrochloride salt.

$^1$H NMR (DMSOd$_3$+CF$_3$COOD, 400 MHz) δ: 3.6–3.7 (2H, m); 6.62 (2H, s); 7.1–7.9 (8H, m); 9.06 (1H, s).

EXAMPLE 38

(2S)-2-{4-[(E)-3-(1-Methylimidazol-5-yl)prop-1-en-1-yl]-2-(4-fluorophenyl)benzamido}-4-methylsulfanylbutyric Acid The title compound was prepared from Example 39 as described for Example 1.

$^1$H NMR (DMSO+CF$_3$COOD, 400 MHz) δ: 1.74–2.03 (2H, m); 2.01 (3H, s); 3.69 (2H, d); 3.81 (3H, s); 4.28–4.35 (1H, dd); 6.50–6.66 (2H, m); 7.13–7.24 (2H, m); 7.37–7.60 (6H, m); 9.06 (1H, s).

| Anal. Calculated for C$_{25}$H$_{26}$FN$_3$O$_3$S, 1.2 H$_2$O | C 61.38 | H 5.85 | N 8.59 | S 6.55 |
|---|---|---|---|---|
| Found | C 61.00 | H 5.94 | N 8.57 | S 6.53 |

MS (ESI) m/z: 468 (MH$^+$).

EXAMPLE 39 tert-Butyl (2S)-2-{4-[(E)-3-(1-methylimidazol-5-yl)prop-1-en-1-yl]-2-(4-fluorophenyl)benzamido}-4-methylsulfanylbutyrate The title compound was prepared from 4-[3-(1-methylimidazol-5-yl)prop-1-en-1-yl]-2-(4-fluorophenyl)benzoic acid and the appropriate amine as described for Example 2.

$^1$H NMR (CDCl$_3$, 400 MHz) δ: 1.42 (9H, s); 1.72–1.88 (1H, m); 1.89–2.02 (1H, m); 2.04 (3H, s); 2.14–2.26 (2H, m); 3.52 (2H, d); 3.57 (3H, s); 4.50–4.57 (1H, m); 5.97 (1H, d); 6.35–6.43 (2H, m); 6.80–7.52 (8H, m); 7.62 (1H, d).

| Anal. Calculated for C$_{29}$H$_{34}$FN$_3$O$_3$S, 0.6 H$_2$O | C 65.17 | H 6.64 | N 7.86 | S 6.00 |
|---|---|---|---|---|
| Found | C 65.14 | H 6.97 | N 7.89 | S 6.46 |

MS (ESI) m/z: 524 (MH$^+$).

The starting material was prepared as follows:

Methyl 4-[3-(1-methylimidazol-5-yl)prop-1-en-1-yl]-2-(4-fluorophenyl)benzoate was prepared from methyl 4-(3-bromoprop-1-en-1-yl)-2-(4-fluorophenyl)benzoate and 5-iodo-1-methyl-imidazole using a similar method to that described for methyl 4-[(E)-3-(1-tritylimidazol-5-yl)prop-1-en-1-yl]-2-(4-fluorophenyl)benzoate in Example 37.

Yield: 59%; MS (ESI) m/z: 351 (MH$^+$).

4-[3-(1-Methylimidazol-5-yl)prop-1-en-1-yl]-2-(4-fluorophenyl)benzoic acid was prepared from methyl 4-[3-(1-methylimidazol-5-yl)prop-1-en-1-yl]-2-(4-fluorophenyl)benzoate using a similar method to that described for 4-[(E)-3-(imidazol-5-yl)prop-1-en-1-yl]-2-(4-fluorophenyl)benzoic acid in Example 37.

MS (ESI) m/z: 337 (MH$^+$).

EXAMPLE 40

(2S)-2-{4-[(E)-3-(1-Benzylimidazol-2-yl)prop-1-en-1-yl]-2-(4-fluorophenyl)benzamido}-4-methylsulfanylbutyric Acid The title compound was prepared from Example 41 as described for Example 1.

$^1$H NMR (DMSO, 400 MHz) δ: 1.7–2.1 (2H, m); 2.01 (3H, s); 2.1–2.4 (2H, m); 4.02 (2H, d); 4.32 (1H, m); 5.49 (2H, s); 6.26–6.44 (1H, m); 6.60 (1H, d); 7.13–7.61 (12H, m); 7.72 (1H, d); 7.77 (1H, d).

| Anal. Calculated for C$_{31}$H$_{30}$FN$_3$O$_3$S  1.5  H$_2$O | C 65.24 | H 5.83 | N 7.36 |
|---|---|---|---|
| Found | C 65.04 | H 5.42 | N 7.21 |

MS (ESI) m/z: 544 (MH$^+$).

EXAMPLE 41 tert-Butyl (2S)-2-{4-[(E)-3-(1-Benzylimidazol-2-yl)prop-1-en-1-yl]-2-(4-fluorophenyl)benzamido}-4-methylsulfanylbutyrate The title compound was prepared from 4-[3-(1-benzylimidazol-2-yl)prop-1-en-1-yl]-2-(4-fluorophenyl)benzoic acid and the appropriate amine as described for Example 2.

Yield: 17%; $^1$H NMR (CDCl$_3$, +CF$_3$COOD, 400 MHz) δ: 1.46 (9H, s); 1.7–2.3 (4H, m); 2.05 (3H, s); 3.95 (2H, d); 4.56–4.64 (1H, m); 5.28 (2H, s); 6.12–6.24 (1H, m); 6.55 (1H, d); 6.98–7.60 (14H, m).

| Anal. Calculated for C$_{35}$H$_{38}$FN$_3$O$_3$S  0.6 H$_2$O | C 68.85 | H 6.47 | N 6.88 | S 5.25 |
|---|---|---|---|---|
| Found | C 68.83 | H 6.68 | N 7.18 | S 5.50 |

MS (ESI) m/z: 601 (MH$^+$).

The starting material was prepared as follows:

Methyl 4-[3-(1-benzylimidazol-2-yl)prop-1-en-1-yl]-2-(4-fluorophenyl)benzoate was prepared from methyl 4-(3- bromoprop-1-en-1-yl)-2-(4-fluorophenyl)benzoate as described for methyl 4-[3-(1-methylimidazol-2-yl)prop-1-en-1-yl]-2-(4-fluorophenyl)benzoate in Example 19, but using N-benzylimidazole. Yield: 76%

¹H NMR (CDCl₃, +CF₃COOD, 400 MHz) δ: 3.69 (3H, s); 4.01 (2H, m); 5.28 (2H, s); 6.14 (1H, m); 6.52 (1H, m); 7.0–7.9 (14H, m). MS (ESI) m/z: 427 (MH⁺).

A solution of methyl 4-[3-(1-benzylimidazol-2-yl)prop-1-en-1-yl]-2-(4-fluorophenyl)benzoate (3 g; 7 mmol), sodium hydroxide (0.8 g; 20 mmol) and distilled water (5 ml) in methanol (50 ml) was refluxed for 4 hours. After evaporation to dryness and acidification to pH 6 with 6N HCl, the resulting solid was triturated with water and ether to give 4-[3-(1-benzylimidazol-2-yl)prop-1-en-1-yl]-2-(4-fluorophenyl)benzoic acid as a mixture of E and Z isomers.

¹H NMR (DMSO, 400 MHz) δ: 4.04 (2H, m); 5.50 (2H, s); 6.3–7.9 (16H, m). MS (ESI) m/z: 413 (MH⁺).

EXAMPLE 42

(2S)-2-{4-[(E)-3-(Imidazol-1-yl)prop-1-en-1-yl]-2-(4-fluorophenyl)benzamido}-4-methylsulfanylbutyric Acid A solution of tert-butyl (2S)-2-{4-[(E)-3-(imidazol-1-yl)prop-1-en-1-yl]-2-(4-fluorophenyl)benzamido}-4-methylsulfanylbutyrate (0.2 g; 0.4 mmol) in dichloromethane (2 ml) was treated at 0° C. with TFA (2 ml). The mixture was allowed to warm to ambient temperature and stirred for 1 hour. After evaporation of the solvent, the residue was taken up with distilled water (5 ml); the pH was adjusted to 6 with NH₄OH and the solution was purified on reverse phase silica eluting with methanol/ammonium carbonate buffer (2 g/l; pH 7) (40/60) to give the title compound after freeze-drying. Yield: 40%

¹H NMR (DMSO+CF₃COOD, 400 MHz) δ: 1.8–2 (2H, m); 2 (3H, s); 2.15–2.4 (2H, m); 4.32 (1H, m); 5.05 (2H, m); 6.6–6.85 (2H, m); 7.20 (2H, m); 7.4–7.6 (5H, m); 7.7–7.85 (2H, m); 9.21 (1H,s).

| Anal. Calculated for C₂₄H₂₄N₃O₃SF  1.11 H₂O | C 60.90 | H 5.58 | N 8.88 | S 6.77 |
|---|---|---|---|---|
| Found | C 60.80 | H 5.32 | N 8.83 | S 6.37 |

MS (FSI) m/z: 454 (MH⁺).

EXAMPLE 43

(2S)-2-{4-[(E)-3-(Imidazol-1-yl)prop-1-en-1-yl]-2-(4-fluorophenyl)benzamido}-4-methylsulfanylbutan-1-ol A solution of lithium borohydride (0,066 g; 3 mmol) in diethyl ether (15 ml) was added at 0° C. to a solution of Example 2 (0,74 g, 1.6 mmol) in THF (40 ml). After stirring at ambient temperature overnight the mixture was acidified at pH 8 with 12N HCl and evaporated to dryness. The residue was taken up in dichloromethane/methanol (90/10). After evaporation of the solvent, the compound was purified on reverse phase silica eluting with methanol/ammonium carbonate (2 g/l pH 7) buffer. The appropriate fractions were concentrated under vacuum and extracted with dichloromethane and evaporated to give the title compound as a solid. Yield: 36%

¹H NMR (CDCl₃, 400 MHz) δ: 1.4–1.8 (2H, m); 2.04 (3H, s); 2.2–2.4 (2H, m); 3.48 (2H, m); 4.02 (1H, m); 4.74 (2H, m); 5.62 (1H, d); 6.3–6.6 (2H, m); 6.96 (1H, m); 7–7.77 (9H, m).

| Anal. Calculated for C₂₄H₂₆FNSO₂S, 0.4  H₂O | C 64.52 | H 6.07 | N 9.41 | S 7.18 |
|---|---|---|---|---|
| Found | C 64.75 | H 6.10 | N 9.50 | S 7.23 |

MS (ESI) m/z: 440 (MH⁺).

EXAMPLE 44

(3S)-3-{4-[(E)-3-(Imidazol-1-1-yl)prop-1-en-1-yl]-2-(4-fluorophenyl)benzamido}-5-methylsulfanyl-1-phenyl-2-pentanone A mixture of 4-[(E)-3-(imidazol-1-yl)prop-1-en-1-yl]-2-(4-fluorophenyl)benzoic acid (0.65 g, 2 mmol), (2S)-3-amino-5-methylsulfanyl-1-phenyl-2-pentanone (0.62 g, 2.4 mmol), HOBT (0.3 g, 2.2 mmol), EDC (0.425 g, 2.2 mmol), DMAP (0.245 g, 2 mmol) in dichloromethane (20 ml) was stirred at room temperature overnight. The reaction mixture was extracted with dichloromethane, evaporated to dryness and purified by flash chromatography eluting with dichloromethane/ethanol (97/3) to give the title compound. Yield: 35%

¹H NMR (CDCl₃, 400 MHz) δ: 1.7–1.9 (2H, m); 2.05 (3H, s); 2–2.2 (2H, m); 3.78 (2H, m); 4.7–4.9 (3H, m); 6.12 (1H, m); 6.30–6.6 (2H, m); 6.96 (1H, s); 7–7.7 (14H, m).

| Anal. Calculated for C₃₁H₃₀FNO₃O₂S, 0.4 distilled water | C 69.61 | H 5.80 | N 7.86 | S 5.99 |
|---|---|---|---|---|
| Found | C 69.79 | H 5.80 | N 8.00 | S 6.37 |

MS (ESI) m/z: 528 (MH⁺).

The starting material was prepared as follows:

A solution of DEBAL in hexane (440 ml) was added dropwise at −70° C. under argon atmosphere to a suspension of ethyl 2-(imidazol-1-yl)acetate (27.13 g; 0. 176 mole) in ether (1.21). The mixture was stirred at −70° C. for 2 hours 30 minutes. Methanol (100 ml) and distilled water (8 ml) were then added at −70° C. and the mixture was allowed to warm to ambient temperature and stirred for 2 hours. The resulting precipitate was filtered, washed with dichloromethane/methanol (2×400 ml) and the filtrate was evaporated and purified by flash chromatography eluting with a gradient 10–25% methanol/dichloromethane to give 2-(imidazol-1-yl)acetaldehyde which was isolated as the hemiacetal 2-(imidazol-1-yl)-1-methoxyethanol. Yield: 68%

¹H NMR (CDCl₃, 400 Hz) δ: 3.48 (3H, s); 4.02 (2H, d); 6.9–7.5 (3H, m).

A solution of 2-(imidazol-1-yl)acetaldehyde (2.6 g; 0.0 18 mmol), 3-(4-fluorophenyl)-4-methoxycarbonylbenzyl triphenylphosphonium bromide (5.4 g; 0.09 mmol), potassium carbonate (1.38 g; 0.01 mmol) and 18 crown-6 (0.1 g; 0.37 mmol) in THF (150 ml) was stirred under argon atmosphere at ambient temperature overnight. After filtration of the insoluble material and evaporation to dryness, the residue was purified by flash chromatography eluting with a mixture of dichloromethane/ethanol (98/2) to give methyl 4-[3-(imidazol-1-yl)prop-1-en-1-yl]-2-(4-fluorophenyl)benzoate as a mixture of E and Z isomers. Yield: 93%

A solution of methyl 4-[3-(imidazol-1-yl)prop-1-en-1-yl]-2-(4-fluorophenyl)benzoate (E and Z isomers) (1.9 g; 5.6 mmol) and 2N aqueous sodium hydroxide solution (8.5 ml; 17 mmol) in methanol (100 ml) was refluxed for 9 hours.

After evaporation and acidification with 12N HCl (1.5 ml), the resulting solid was washed with distilled water and ether, taken up in dichloromethane/methanol (99/1) to give 4-[(E)-3-(imidazol-1-yl)prop-1-en-1-yl]-2-(4-fluorophenyl)benzoic acid (E isomer) after evaporation as a foam. Yield: 89%.

$^1$H NMR (DMSO+CF$_3$COOD, 400 MHz) δ: 5.06 (2H, d); 6.7–7.85 (2H, m); 7.1–7.9 (9H, m); 9.22 (1H, s).

EXAMPLE 45

(3S)-3-{5-[(Z)-3-(Imidazol-1-yl)prop-1-en-1-yl]-2-(4-fluorophenethyl)benzamido}-5-methylsulfanyl-1-phenyl-2-pentanone A solution of pentafluorophenyl 5-[(Z)-3-(imidazol-1-yl)prop-1-en-1-yl]-2-(4-fluorophenethyl)benzoate (0.25 g, 0.5 mmol), (3S)-5-methylsulfanyl-2-oxo-1-phenylpentan-3amine (0.16 g, 0.6 mmol), 1-hydroxy-7-azabenzotriazole (0.075 g, 0.55 mmol) in DMF (2 ml) was stirred at ambient temperature overnight. After evaporation of the solvent, the residue was taken up in ethyl acetate, washed with 5% sodium hydrogen carbonate and saturated sodium chloride and evaporated to dryness. The residue was then purified by flash chromatography eluting with dichloromethane/ethanol (97/3) to give the title compound which was isolated as the hydrochloride salt by treatment with HCl/ether. Yield: 70%

$^1$H NMR (DMSOd$_6$+CF$_3$COOD, 400 MHz) δ: 1.83–2.20 (2H, m); 2.04 (3H, s); 2.05–3.11 (6H, m); 3.99 (2H, s); 4.74 (1H, dd); 5.23 (2H, d); 5.85–5.96 (1H, m); 6.99–7.10 (2H, m); 7.13–7.44 (10H, m); 7.73 (1H, s); 7.78 (1H, s); 9.21 (1H, s).

| Anal. Calculated for C$_{33}$H$_{34}$FN$_3$O$_2$S 1.25 HCl | C 65.92 | H 5.91 | N 6.99 | S 5.33 | Cl 7.37 |
|---|---|---|---|---|---|
| Found | C 66.03 | H 6.20 | N 6.97 | S 5.57 | Cl 7.56 |

MS (ESI) m/z: 556 (MH$^+$).

The starting material was prepared as follows:

A solution of 2-(imidazol-1-yl)acetaldehyde (2.8 g; 0.021 mmol), 4-(4-fluorophenethyl)-3-methoxycarbonylbenzyl triphenylphosphonium bromide (6.2 g; 0.01 mmol), potassium carbonate (2.8 g; 0.02 mmol) and 18 crown-6 (0.1 g; 0.37 mmol) in dichloromethane (100 ml) was stirred under argon atmosphere at ambient temperature overnight. After extraction and evaporation to dryness, the residue was purified by flash chromatography eluting with a mixture of dichloromethane/ethanol (98/2) to give methyl 5-[3-(imidazol-1-yl)prop-1-en-1-yl]-2-(4-fluorophenethyl)benzoate as a mixture of E and Z isomers.

Yield: 70%; $^1$H NMR (CDCl$_3$, 400 MHz) δ: 2.8–2.95 (2H, m); 3.15–3.30 (2H, m); 3.89 and 3.91 (3H, s); 4.7–4.85 (2H, m); 5.8–6.8 (2H, m); 6.9–7.85 (10H, m).

A solution of methyl 5-[3-(imidazol-1-yl)prop-1-en-1-yl]-2-(4-fluorophenethyl)benzoate (E and Z isomers) (2.4 g; 6.6 mmol) in methanol (100 ml) was treated with a solution of sodium hydroxide (0.8 g; 20 mmol) in water (3 ml). The mixture was refluxed for 9 hours. After evaporation and acidification with 12N HCl (1.5 ml), the residue was extracted with dichloromethane to give after evaporation 5-[3-(imidazol-1-yl)prop-1-en-1-yl]-2-(4-fluorophenethyl)benzoic acid as a mixture of E and Z isomers.

$^1$H NMR (DMSOd$_6$+CF$_3$COOD) 400 MHz) δ: 2.75–2.90 (2H, m); 3.1–3.3 (2H, m); 4.95–5.30 (2H, m); 5.90 and 6.5–6.85 (2H, m); 7–7.95 (10H, m); 9.2 (1H, m). MS (ESI) m/z: 351 (MH$^+$).

Pentafluorophenyl trifluoroacetate (1.47 ml; 8.6 mmol) was added to a solution of 5-[3-(imidazol-1-yl)prop-1-en-1-yl]-2-(4-fluorophenethyl)benzoic acid (2.5 g, 7.14 mmol) and pyridine (0.7 ml; 8.6 mmol) in DMF (7 ml). After stirring at ambient temperature overnight, the mixture was evaporated to dryness and the residue extracted with ethyl acetate, washed with saturated sodium hydrogen carbonate and saturated sodium chloride. After evaporation the reaction mixture was purified by flash chromatography eluting with dichloromethane/ethanol (99/1) to give E isomer pentafluorophenyl 5-[(E)-3-(imidazol-1-yl)prop-1-en-1-yl]-2-(4-fluorophenethyl)benzoate and Z isomer pentafluorophenyl 5-[(Z)-3-(imidazol-1-yl)prop-1-en-1-yl]-2-(4-fluorophenethyl)benzoate. Yield: 68%

E isomer: $^1$H NMR (CDCl$_3$, 400 MHz) δ: 2.88 (2H, m); 3.26 (2H, m); 4.76 (2H, m); 6.3–6.6 (2H, m); 6.9–7.8 (9H, m); 8.17 (1H, d).

Z isomer: $^1$H NMR (CDCl$_3$, 400 MHz) δ: 2.90 (2H, m); 3.27 (2H, m); 4.82 (2H, m); 5.89 (1H, m); 6.78 (1H, m); 6.9–7.6 (9H, m); 8.07 (1H, s).

EXAMPLE 46

(3S)-3-{5[(E)-3-(Imidazol-1-yl)prop-1-en-1-yl]-2-(4-fluorophenethyl)benzamido}-5-methylsulfanyl-1-phenyl-2-pentanone The title compound was prepared from pentafluorophenyl 5-[(E)-3-(imidazol-1-yl)prop-1-en-1-yl]-2-(4-fluorophenethyl)benzoate using a similar method to that described in Example 3 and isolated as the hydrochloride salt by treatment with HCl/ether. Yield: 42%

$^1$H NMR (DMSOd$_6$+CF$_3$COOD, 400 MHz) δ: 1.83–2.19 (2H, m); 2.04 (3H, s); 2.50–3.07 (6H, m); 3.98 (2H, s); 4.73 (1H, dd); 5.04 (2H, d); 6.46–6.59 (1H, m); 6.76 (1H, d); 6.96–7.11 (2H, m); 7.12–7.37 (9H, m); 7.48 (1H, s); 7.74 (1H, s); 7.80 (1H, s); 9.22 (1H, s).

| Anal. Calculated for C$_{33}$H$_{34}$FN$_3$O$_2$S, 1.5 HCl | C 64.93 | H 5.86 | N 6.88 | S 5.25 | Cl 8.71 |
|---|---|---|---|---|---|
| Found | C 66.15 | H 6.21 | N 6.89 | S 5.78 | Cl 8.74 |

MS (ESI) m/z: 556 (MH$^+$).

EXAMPLE 47

1-Methylpiperidin-4-yl(2S)-2-[(3-(4-fluorophenyl)-5-[(E)-3-(1H-imidazol-1-yl)prop-1-enyl]-2-thienylcarbonyl)amino]-4-(methylsulfanyl)butanoate A solution of 1-[3-(4-fluorophenyl)-5-[(E)-3-(1H-imidazol-1-yl)prop-1-enyl]-thien-2-yl]methanoic acid (4.2 g; 12.8 mmol), EDC (3.19 g; 16.6 mmol) and DMAP (0.313 g; 2.6 mmol) in DMF (50 ml) was stirred under argon atmosphere for 15 minutes. 1-(Methylpiperidin-4-yl)-4-(methylsulfanyl) butanoate (5.27 g; 16.6 mmol) and N-methylmorpholine (3.65 ml; 32.2 mmol) were then added. The mixture was stirred at room temperature overnight. After evaporation to dryness, the residue was taken up in CH$_2$Cl$_2$/H$_2$O and extracted. The organic phase was evaporated and purified by preparative HPLC on reverse phase silica eluting with MeOH/(NH$_4$)2CO$_3$ buffer (2 g/l, pH 7) 50/50 to give after evaporation of the appropriate fractions a solid which was redissolved in CH$_2$Cl$_2$/ether and treated at 0° C. with a solution of HCl/ether. After 10 minutes the resulting solid was filtered, washed with ether and dried to give the desired product. Yield: 14%

¹H NMR (DMSOd₆+TFA, 400 MHz) δ: 1.8–2.2 (6H, m); 2.0 (3H, m); 2.3–2.6 (2H, m); 2.78 (3H, s); 2.9–3.2 (2H, m); 3.25–3.5 (2H, m); 4.3–4.5 (1H, m); 4.8–5.2 (2H, m); 5.05 (2H, m); 6.4 (1H, m); 6.8 (1H, d); 7.2–7.6 (5H, m); 7.74 (2H, m); 9.2 (1H, s).

| Anal. calculated for $C_{28}H_{33}N_4O_3S_2F$, 2 HCl, 0.6 $H_2O$ | C 52.23 | H 5.78 | N 8.61 | S 9.31 | Cl 11.15 |
|---|---|---|---|---|---|
| Found | C 52.51 | H 5.70 | N 8.75 | S 10.01 | Cl 11.07 |

MS (ESI) m/s: 557 (MH⁺).

1-[3-(4-Fluorophhenyl)-5-[(E)-3-(1H-imidazol-1-yl) prop-1-enyl]-thien-2-yl]methanoic Acid The starting material was prepared as follows:

To a solution of methyl 1-[5-methyl-3-hydroxy-thien-2-yl]methanoate (53.5 g; 0.311 mmol) in pyridine (11), cooled at 0° C. was added dropwise triflic anhydride (67.83 ml; 0.40 mmol). After stirring at 0° C. for 1 hour and then at room temperature for 1 hour, the mixture was evaporated to dryness and the residue extracted with $CH_2Cl_2/H_2O$. The organic phase was evaporated and purified by flash chromatography, eluting with petroleum ether/ethylacetate 95/5 to give methyl 1-[5-methyl-3-triflate-thien-2-yl]methanoate.

Yield:90%; ¹H NMR (CDCl₃, 400 MHz) δ: 2.51 (3H, s); 3.89 (3H, s); 6.71 (1H, s).

To a solution of methyl 1-[5-methyl-3-triflate-thien-2-yl]methanoate (10 g; 0.033 mol) in a mixture of toluene (11) and ethanol (100 ml) was added 4-fluorobenzene boronic acid (6.9 g; 0.049 mol), $Na_2CO_3$ 2M (41 ml; 0.082 mol), LiCl (2.79 g; 0.066 mol) and tetrakis(triphenylphosphine) palladium(0) (1.52 g; 0.013 mmol). The mixture was refluxed under argon atmosphere for 2 h 30, extracted with ethyl acetate and purified by flash chromatography eluting with petroleum ether/AcOEt 95/5 to give after evaporation and trituration in ether to give methyl 1-[5-methyl-3-(4-fluorophenyl)-thien-2-yl]methanoate as a white solid.

Yield: 79%; ¹H NMR (CDCl₃, 400 MHz) δ: 2.51 (3H, s); 3.74 (3H, s); 6.75 (1H, s); 7.06 (2H, m); 7.40 (2H, m).

A solution of methyl 1-[5-methyl-3-(4-fluorophenyl)-thien-2-yl]methanoate (12.9 g; 0.05 mol), N-bromosuccinimide (11.02 g; 0.0619 mol) and 2-2'-azobisisobutyronitrile (0.339 g; 2.06 mmol) in $Cl_4$ (300 ml) was reflux under argon atmosphere for 90 minutes under UV irradiation. After filtration of the precipitate, the filtrate was evaporated to dryness to give methyl 1-[5-bromomethyl-3-(4-fluorophenyl)-thien-2-yl]methanoate as a solid which was used in the next step without purification.

¹H NMR (CDCl₃, 400 MHz) δ: 3.77 (3H, s); 4.65 (2H, s); 7.06 (3H, m); 7.40 (2H, m).

A solution of methyl 1-[5-bromomethyl-3-(4-fluorophenyl)-thien-2-yl]methanoate (10.6 g; 0.032 mol) and triphenylphosphine (8.95 g; 0.035 mol) in toluene (200 ml) was refluxed under argon atmosphere for 4 hours. After cooling, the precipitate was filtered, washed with toluene and petroleum ether and dried to give methyl 1-[5-triphenylphosphine-3-(4-fluorophenyl)-thien-2-yl]methanoate.

Yield: 93%; ¹H NMR (CDCl₃, 400 MHz) δ: 3.66 (3H, s); 6.08 (2H, d); 7.05 (2H, m); 7.1–7.3 (3H, m); 7.6–8 (15H, m).

To a solution of methyl 1-[5-tri-phenylphosphine-3-(4-fluorophenyl)-thien-2-yl]methanoate (17.6 g; 0.03 mol) and 2-(imidazol-1-yl)acetaldehyde (8.46 g; 0.06 mol) in $CH_2Cl_2$ (250 ml was added under argon atmosphere, potassium t-butylate (3.34 g; 0.03 mol). The mixture was stirred at room temperature for 3 hours, evaporated and purified by flash chromatography eluting with ethyl acetate and then with $CH_2Cl_2$/MeOH 95/5 to give after trituration in ether methyl 1-[5-(3-(1H-imidazol-1-yl)prop-1-enyl)-3-(4-fluorophenyl)-thien-2-yl]methanoate a solid.

Yield: 54%; ¹H NMR (CDCl₃, 400 MHz) δ: 3.79 (3H, s); 5.0 (2H, d); 5.87 (1H, m); 6.72 (1H, m); 6.9–7.8 (8H, m).

A solution of methyl 1-[5-[(E)-3-(1H-imidazol-1-yl)prop-1-enyl]-3-(4-fluorophenyl)-thien-2-yl]methanoate (9 g; 0.026 mol) in methanol (100 ml) was treated with 2N aqueous sodium hydroxide solution (39.5 ml; 0.079 mol). The mixture was heated at 60° C. for 1 hour and evaporated. The residue was taken up in water (100 ml)/ether (100 ml). The aqueous phase was acidified with HCl 2N to pH 5 and the resulting precipitate was filtered, washed with $H_2O$, dried over $P_2O_5$ and triturated in ether to 1-[3-(4-fluorophenyl)-5-[(E)-3-(1H-imidazol-1-yl)prop-1-enyl]-thienyl]methanoic acid as a solid.

Yield: 66%; ¹H NMR (CDCl₃, 400 MHz) δ: 6.50 (1H, s); 6.86 (1H, m); 7.25 (3H, m); 7.50 (2H, m); 7.74 (1H, m); 7.8 (1H, m); 9.2 (1H, s).

EXAMPLE 48

1-Methylpiperidin-4-yl (2S-[(3-(4-Fluorophenyl-5-[(E)-3-(1H-imidazol-1-yl)prop-1-enyl]-2-thienylcarbonyl)amino]4-(methylsulfanyl)butanoate The compound was prepared using the same methodology as described for example 47 but was purified by flash chromatography eluting with $CH_2Cl_2$/MeOH 98/2.

Yield: 85%; ¹H NMR (CDCl₃, 400 MHz) δ: 1.4 (9H, m); 1.7–2.2 (2H, m); 2.03 (3H, s); 2.25 (2H, m); 4.6 (1H, m); 4.7 (2H, m); 6–6.5 (3H, m); 6.8–7.6 (8H, m). MS (ESI) m/z: 515 (MH⁺).

EXAMPLE 49

(2S)-2-[(3-(4-Fluorophenyl)-5-[(E)-3-(1H-imidazol-1-yl)prop-1-enyl]-2-thienylcarbonyl)amino]-4-(methylsulfanyl)butanoic Acid A solution of example 48 (2 g; 3.88 mmol) in $CH_2Cl_2$ (20 ml) was treated with TFA (20 ml). The mixture was stirred at room temperature for 2 hours. After evaporation, the residue was purified on reverse phase silica eluting with MeOH/$(NH_4)_2$ $CO_3$ buffer (2 g/l, pH 7) 40/60 to give the desired product. Yield: 33%

¹H NMR (DMSO+CF₃COOD, 400 MHz) δ: 1.8–2.1 (2H, m); 2.01 (3H, s); 2.2–2.5 (2H, m); 4.34 (1H, m); 5.02 (2H, d); 6.42 (1H, m); 6.88 (1H, d); 7.1–7.4 (3H, m); 7.52 (2H, m); 7.77 (2H, m); 9.19 (1H, s).

| Anal. calculated for $C_{22}H_{22}N_3O_3S_2F$, 0.6 $H_2O$, 0.3 ether | C 56.57 | H 5.36 | N 8.53 | S 13.02 |
|---|---|---|---|---|
| Found | C 56.28 | H 5.10 | N 8.71 | S 12.76 |

MS (ESI) m/z: 460 (MH⁺).

What is claimed is:

1. A compound of Formula (1):

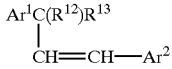

Formula (1)

wherein $Ar^1$ represents:

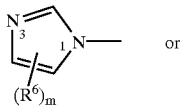

(A)

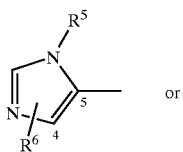

(B)

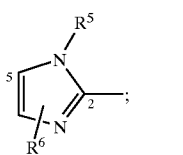

(C)

and wherein $R^5$ is hydrogen, $C_{1-4}$alkyl, phenyl$C_{1-4}$alkyl;

$R^6$ is hydrogen, $C_{1-4}$alkyl, hydroxy$C_{1-4}$alkyl, halo$C_{1-4}$alkyl, dihalo$C_{1-4}$alkyl, $C_{1-4}$alkoxy, $C_{1-4}$alkoxy$C_{1-4}$alkyl, sulfanyl$C_{1-4}$alkyl, amino$C_{1-4}$alkyl, N—($C_{1-4}$alkyl)amino$C_{1-4}$alkyl, N,N-di($C_{1-4}$alkyl)amino$C_{1-4}$alkyl or phenyl$C_{1-4}$alkyl; and m is 0, 1 or 2;

$R^{12}$ and $R^{13}$ are independently hydrogen or $C_{1-4}$alkyl; and $Ar^2$ is phenyl, pyridyl, pyridazinyl, pyrimidyl, pyrazinyl, thienyl, thiazolyl, furyl or oxazolyl, the ring being substituted on ring carbon atoms by $R^2$ and —$(CH_2)_n$ $R^3$, wherein $Ar^2$ is attached to $Ar^1C(R^{12})R^{13}CH=CH—$ by a ring carbon atom; or $Ar^2$ is pyrrolyl, pyrazolyl or imidazolyl, the ring being substituted on ring carbon atoms or on the $sp^3$ hybridised ring nitrogen by $R^2$ and —$(CH_2)_nR^3$, wherein $Ar^2$ is attached to $Ar^1C(R^{12})R^{13}CH=CH—$ by a ring carbon atom or the $Sp^3$ hybridised ring nitrogen;

and wherein $R^2$ is a group of the Formula (2):

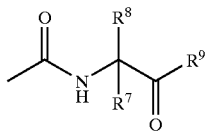

Formula (2)

wherein $R^7$ is hydrogen or $C_{1-4}$alkyl, $R^8$ is —$(CH_2)_q$—$R^{10}$ wherein q is 0–4 and $R^{10}$ is $C_{1-4}$alkylsulfanyl, $C_{1-4}$alkylsulfinyl, $C_{1-4}$alkylsulfonyl, hydroxy, $C_{1-4}$alkoxy, carbamoyl, N—$C_{1-4}$alkyl carbamoyl, N,N-(di$C_{1-4}$alkyl)carbamoyl, $C_{1-4}$alkyl, phenyl, thienyl, or $C_{1-4}$alkanoylamino, $R^9$ is hydroxy, $C_{1-6}$alkoxy, $C_{3-9}$cycloalkyloxy, heterocyclyloxy, heterocyclyl$C_{1-4}$alkoxy or —NH—$SO_2$-$R^{11}$ wherein $R^{11}$ represents trifluoromethyl, $C_{1-4}$alkyl, phenyl, heteroaryl, aryl$C_{1-4}$alkyl or heteroaryl$C_{1-4}$alkyl;

or $R^2$ represents a lactone of Formula (3)

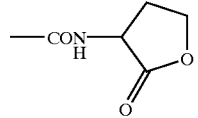

Formula (3)

the group of Formula (2) or (3) having L or D configuration at the chiral alpha carbon in the corresponding free amino acid;

or $R^2$ is a group of the Formula (4):

Formula (4)

wherein $R^{14}$ is —$(CH_2)_q$—$R^{16}$ wherein q is 0–4 and $R^{16}$ is $C_{1-4}$alkylsulfanyl, $C_{1-4}$alkylsulfinyl, $C_{1-4}$alkylsulfonyl, hydroxy, $C_{1-4}$alkoxy, carbamoyl, N—$C_{1-4}$alkylcarbamoyl, N,N-(di$C_{1-4}$alkyl)carbamoyl, $C_{1-4}$alkyl, phenyl, thienyl, or $C_{1-4}$alkanoylamino; $R^{15}$ is of the formula —$CH_2OR^{17}$ (wherein $R^{17}$ is hydrogen, $C_{1-4}$alkyl, phenyl, heteroaryl, $C_{2-5}$alkanoyl, $C_{1-4}$alkoxymethyl, phenoxymethyl or heteroaryloxymethyl), of the formula —$COR^{18}$ or of the formula —$CH_2COR^{18}$ (wherein $R^{18}$ is $C_{1-4}$alkyl (optionally substituted by halo, cyano, $C_{2-5}$alkanoyloxy, hydroxy, $C_{1-4}$alkoxy or $C_{1-4}$alkanoyl), phenyl, phenyl$C_{1-3}$alkyl, heteroaryl, heteroaryl$C_{1-3}$alkyl, $C_{5-7}$cycloalkyl, $C_{5-7}$cycloalkyl$C_{1-3}$alkyl, 2-(phenyl)ethenyl, 2-(heteroaryl)ethenyl or N-methoxy-N-methylamino); or $R^{15}$ is morpholino$C_{1-4}$alkyl, pyrrolidin-1-yl$C_{1-4}$alkyl or piperidin-1-yl$C_{1-4}$alkyl wherein the morpholine, pyrrolidine and piperidine rings are optionally substituted by $C_{1-4}$alkyl or $C_{5-7}$cycloalkyl; or $R^{15}$ is phenyl-1-hydroxy$C_{1-4}$alkyl or heteroaryl-1-hydroxy$C_{1-4}$alkyl;

n is 0, 1 or 2; and $R^3$ is phenyl or heteroaryl; and wherein phenyl and heteroaryl rings in $R^3$, $R^5$, $R^6$, $R^{11}$, $R^{15}$ (including $R^{17}$ and $R^{18}$) are independently optionally substituted on ring carbon atoms by up to three substituents selected from $C_{1-4}$alkyl, halogen, hydroxy, $C_{1-4}$alkoxy, $C_{1-4}$alkoxycarbonyl, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, thiol, $C_{1-4}$alkylsulfanyl, $C_{1-4}$alkylsulfinyl, $C_{1-4}$alkylsulfonyl, $C_{1-4}$alkanesulphonamido, N—($C_{1-4}$alkylsulphonyl)—N—$C_{1-4}$alkylamino, aminosulfonyl, N—($C_{1-4}$alkyl)aminosulfonyl, N,N-di($C_{1-4}$alkyl)aminosulfonyl, carbamoyl, N—($C_{1-4}$alkyl)carbamoyl, N,N-(di$C_{1-4}$alkyl)carbamoyl, carbamoyl$C_{1-4}$alkyl, N—($C_{1-4}$alkyl)carbamoyl$C_{1-4}$alkyl, N,N-(di$C_{1-4}$alkyl)carbamoyl$C_{1-4}$alkyl, hydroxy$C_{1-4}$alkyl and $C_{1-4}$alkoxy$C_{1-4}$alkyl and on ring NH groups (replacing hydrogen) by $C_{1-4}$alkyl, $C_{1-4}$alkanoyl, $C_{1-4}$alkylsulfonyl, halo$C_{1-4}$alkyl, difluoromethyl or trifluoromethyl;

or a pharmaceutically-acceptable salt, prodrug or solvate thereof.

2. A compound of Formula (1):

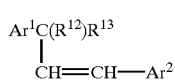

Formula (1)

wherein $Ar^1$ represents:

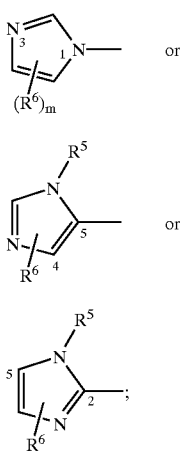

and wherein $R^5$ is hydrogen, $C_{1-4}$alkyl, phenyl$C_{1-4}$alkyl;

$R^6$ is hydrogen, $C_{1-4}$alkyl, hydroxy$C_{1-4}$alkyl, halo$C_{1-4}$alkyl, dihalo$C_{1-4}$alkyl, $C_{1-4}$alkoxy, $C_{1-4}$alkoxy$C_{1-4}$alkyl, sulfanyl$C_{1-4}$alkyl, amino$C_{1-4}$alkyl, N—($C_{1-4}$alkyl)amino$C_{1-4}$alkyl, N,N-di($C_{1-4}$alkyl)amino$C_{1-4}$alkyl or phenyl$C_{1-4}$alkyl; and m is 0, 1 or 2;

$R^{12}$ and $R^{13}$ are independently hydrogen or $C_{1-4}$alkyl; and $Ar^2$ is phenyl, pyridyl or thienyl, the ring being substituted on ring carbon atoms by $R^2$ and —$(CH_2)_n$R and wherein $Ar^2$ is attached to $Ar^1C(R^{12})R^{13}CH=CH$— by a ring carbon atom; and wherein $R^2$ is a group of the Formula (2):

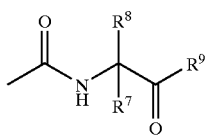

Formula (2)

wherein $R^7$ is hydrogen, $R^8$ is —$(CH_2)_2$—$R^{10}$ wherein $R^{10}$ is $C_{1-4}$alkylsulfanyl or $C_{1-4}$alkylsulfonyl, $R^9$ is hydroxy, $C_{1-6}$alkoxy, $C_{3-9}$cycloalkyloxy, heterocyclyloxy or heterocyclyl$C_{1-4}$alkoxy;

or $R^2$ represents a lactone of Formula (3)

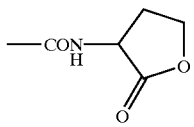

Formula (3)

the group of Formula (2) or (3) having L or D configuration at the chiral alpha carbon in the corresponding free amino acid;

or $R^2$ is a group of the Formula (4):

—CONHCH($R^{14}$)$R^{15}$      Formula (4)

wherein $R^{14}$ is —$(CH_2)_q$—$R^{16}$ wherein q is 0–4 and $R^{16}$ is $C_{1-4}$alkylsulfanyl, $C_{1-4}$alkylsulfinyl, $C_{1-4}$alkylsulfonyl, hydroxy, $C_{1-4}$alkoxy, carbamoyl, N—$C_{1-4}$alkyl carbamoyl, N,N-(di$C_{1-4}$alkyl)carbamoyl, $C_{1-4}$alkyl, phenyl, thienyl, or $C_{1-4}$alkanoylamino; $R^{15}$ is of the formula —$CH_2OR^{17}$ (wherein $R^{17}$ is hydrogen, $C_{1-4}$alkyl, phenyl, heteroaryl, $C_{2-5}$alkanoyl, $C_{1-4}$alkoxymethyl, phenoxymethyl or heteroaryloxymethyl), of the formula —$COR^{18}$ or of the formula —$CH_2COR^{18}$ (wherein $R^{18}$ is $C_{1-4}$alkyl (optionally substituted by halo, cyano, $C_{2-5}$alkanoyloxy, hydroxy, $C_{1-4}$alkoxy or $C_{1-4}$alkanoyl), phenyl, phenyl$C_{1-3}$alkyl, heteroaryl, heteroaryl$C_{1-3}$alkyl, $C_{5-7}$cycloalkyl, $C_{5-7}$cycloalkyl$C_{1-3}$alkyl, 2-(phenyl)ethenyl, 2-(heteroaryl)ethenyl or N-methoxy-N-methylamino); or $R^{15}$ is morpholino$C_{1-4}$alkyl, pyrrolidin-1-yl$C_{1-4}$alkyl or piperidin-1-yl$C_{1-4}$alkyl wherein the morpholine, pyrrolidine and piperidine rings are optionally substituted by $C_{1-4}$alkyl or $C_{5-7}$cycloalkyl; or $R^{15}$ is phenyl-1-hydroxy$C_{1-4}$alkyl or heteroaryl-1-hydroxy$C_{1-4}$alkyl;

n is 0, 1 or 2; and $R^3$ is phenyl or heteroaryl;

and wherein phenyl and heteroaryl rings in $R^3$, $R^5$, $R^6$ and $R^9$ are independently optionally substituted on ring carbon atoms by up to three substituents selected from $C_{1-4}$alkyl, halogen, hydroxy, $C_{1-4}$alkoxy, $C_{1-4}$alkoxycarbonyl, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, thiol, $C_{1-4}$alkylsulfanyl, $C_{1-4}$alkylsulfinyl, $C_{1-4}$alkylsulfonyl, $C_{1-4}$alkanesulphonamido, N—($C_{1-4}$alkylsulphonyl)—N—$C_{1-4}$alkylamino, aminosulfonyl, N—($C_{1-4}$alkyl)aminosulfonyl, N,N-di($C_{1-4}$alkyl)aminosulfonyl, carbamoyl, N—($C_{1-4}$alkyl)carbamoyl, N,N-(di$C_{1-4}$alkyl)carbamoyl, carbamoyl$C_{1-4}$alkyl, N—($C_{1-4}$alkyl)carbamoyl$C_{1-4}$alkyl, N,N-(di$C_{1-4}$alkyl)carbamoylc $C_{1-4}$alkyl, hydroxy$C_{1-4}$alkyl and $C_{1-4}$alkoxy$C_{1-4}$alkyl and on ring NH groups (replacing hydrogen) by $C_{1-4}$alkyl, $C_{1-4}$alkanoyl, $C_{1-4}$alkylsulfonyl, halo$C_{1-4}$alkyl, difluoromethyl or trifluoromethyl;

or a pharmaceutically-acceptable salt, prodrug or solvate thereof.

3. A compound of Formula (I) as claimed in claim 1 or claim 2 wherein $R^3$ is phenyl.

4. A compound of Formula (I) as claimed in claim 3 wherein substituents on the ring carbon atom(s) of the phenyl ring $R^3$ are selected from $C_{1-4}$alkyl, halo, trifluoromethyl, $C_{1-4}$alkoxy, nitro, cyano and $C_{1-4}$alkoxy$C_{1-4}$alkyl.

5. A compound of Formula (I) as claimed in claim 4 wherein a carbon atom of the phenyl ring of $R^3$ is substituted by fluoro, chloro or cyano.

6. A compound of Formula (I) as claimed in claim 1 or claim 2 wherein n is 0 or 2.

7. A compound of Formula (I) as claimed in claim 1 or claim 2 wherein $R^{12}$ and $R^{13}$ are hydrogen.

8. A pharmaceutical composition comprising a compound of Formula (I), or a pharmaceutically-acceptable salt thereof, as defined in claim 1 or claim 2, with a pharmaceutically-acceptable diluent or carrier.

9. A method of treating a disease or medical condition mediated through farnesylation of CAAX-containing proteins which comprises adminstering to a warm-blooded animal in need thereof an effective amount of a compound according to claim 1 or claim 2.

* * * * *